US009717430B2

United States Patent
Liu et al.

(10) Patent No.: US 9,717,430 B2
(45) Date of Patent: Aug. 1, 2017

(54) REAL-TIME MULTI-FUNCTIONAL ECG SIGNAL PROCESSING SYSTEM, DSPE FOR THE ECG SIGNAL PROCESSING SYSTEM, AND METHOD THEREOF

(71) Applicant: AGENCY FOR SCIENCE, TECHNOLOGY AND RESEARCH, Singapore (SG)

(72) Inventors: Xin Liu, Singapore (SG); Jun Zhou, Singapore (SG)

(73) Assignee: Agency of Science, Technology and Research, Singapore (SG)

( * ) Notice: Subject to any disclaimer, the term of this patent is extended or adjusted under 35 U.S.C. 154(b) by 0 days.

(21) Appl. No.: 14/897,581

(22) PCT Filed: Jun. 12, 2014

(86) PCT No.: PCT/SG2014/000276
§ 371 (c)(1),
(2) Date: Dec. 10, 2015

(87) PCT Pub. No.: WO2014/200438
PCT Pub. Date: Dec. 18, 2014

(65) Prior Publication Data
US 2016/0135705 A1    May 19, 2016

(30) Foreign Application Priority Data

Jun. 12, 2013 (SG) ................. 201304531-5

(51) Int. Cl.
*H03M 1/00* (2006.01)
*A61B 5/04* (2006.01)
(Continued)

(52) U.S. Cl.
CPC ........ *A61B 5/04012* (2013.01); *A61B 5/0428* (2013.01); *A61B 5/0472* (2013.01);
(Continued)

(58) Field of Classification Search
CPC ... A61B 5/0006; A61B 5/02055; A61B 5/021; A61B 5/726; A61B 5/0205; H03M 1/12;
(Continued)

(56) References Cited

U.S. PATENT DOCUMENTS

| 4,296,755 A | * | 10/1981 | Judell | ............... | A61B 5/046 600/518 |
| 6,002,952 A | * | 12/1999 | Diab | ............... | A61B 5/02416 600/310 |

(Continued)

FOREIGN PATENT DOCUMENTS

EP    2 298 164 B1    3/2011

OTHER PUBLICATIONS

PCT International Search Report for PCT Counterpart Application No. PCT/SG2014/000276, 4 pp., (Sep. 30, 2014).
(Continued)

*Primary Examiner* — Linh Nguyen
(74) *Attorney, Agent, or Firm* — Blakely, Sokoloff, Taylor & Zafman LLP

(57) ABSTRACT

An electrocardiogram (ECG) signal processing system is provided. The ECG signal processing system comprises an analog-to-digital converter (ADC) configured to convert an input analog ECG signal into a digital ECG signal, and a digital signal processing engine (DSPE) coupled to the ADC to receive the digital ECG signal. The DSPE is configured to decompose and reconstruct the digital ECG signal. A dynamic system clock source is coupled to the ADC and the DSPE for dynamic signal sampling, the dynamic system clock source clocking the ADC and the DSPE at a first frequency f1 to detect one or more first parameters of the input analog ECG signal and at a second frequency f2 to detect one or more second parameters of the input analog ECG signal.

17 Claims, 19 Drawing Sheets

(51) Int. Cl.
*A61B 5/00* (2006.01)
*A61B 5/0428* (2006.01)
*A61B 5/0472* (2006.01)
*A61B 5/0476* (2006.01)
*G01R 19/25* (2006.01)

(52) U.S. Cl.
CPC .......... *A61B 5/4812* (2013.01); *A61B 5/7203* (2013.01); *A61B 5/0476* (2013.01); *A61B 5/4836* (2013.01); *G01R 19/2509* (2013.01)

(58) Field of Classification Search
CPC ........ H03M 1/127; H03M 1/00; H03M 1/462; H03M 3/498; H03M 1/16
USPC .................................. 341/139, 141, 142, 155
See application file for complete search history.

(56) References Cited

U.S. PATENT DOCUMENTS

| | | | |
|---|---|---|---|
| 6,473,008 B2 | 10/2002 | Kelly et al. | |
| 6,760,623 B2* | 7/2004 | Stahmann | A61N 1/3622 607/9 |
| 7,668,588 B2* | 2/2010 | Kovacs | A61B 5/0404 600/509 |
| 8,560,034 B1* | 10/2013 | Diab | A61B 5/14546 356/41 |
| 8,725,238 B2* | 5/2014 | Liu | A61B 5/0452 600/509 |
| 2009/0028365 A1* | 1/2009 | Nygard | H03M 1/187 381/312 |
| 2009/0131762 A1* | 5/2009 | Pelzek | G04G 7/00 600/301 |
| 2010/0097259 A1* | 4/2010 | Zhang | A61B 5/0402 341/155 |
| 2011/0066054 A1* | 3/2011 | Yazicioglu | A61B 5/04 600/509 |
| 2011/0077538 A1* | 3/2011 | Liu | A61B 5/0452 600/509 |
| 2012/0194372 A1* | 8/2012 | Venkatraman | H03M 3/04 341/143 |
| 2013/0296726 A1* | 11/2013 | Niebauer | A61B 5/0452 600/510 |
| 2014/0309505 A1* | 10/2014 | Euliano | A61B 5/4833 600/302 |

OTHER PUBLICATIONS

PCT Notification of Transmittal of International Preliminary Report on Patentability (Chapter II of the Patent Cooperation Treaty) for PCT Counterpart Application No. PCT/SG2014/000276, 5 pp., (Oct. 12, 2015).

Xin Liu, et al., "Multiple Functional ECG Signal is Processing for Wearable Applications of Long-Term Cardiac Monitoring", IEEE Transactions on Biomedical Engineering, vol. 58, No. 2, pp. 380-389, (Feb. 2011).

D. G. Guo, et al., "A Wearable BSN-based ECG-recording System Using Micromachined Electrode for Continuous Arrhythmia Monitoring", Proceedings of the 5th International Workshop on Wearable and Implantable Body Sensor Networks, pp. 41-44, (Jun. 1-3, 2008).

Jos Hulzink, et al., "An Ultra Low Energy Biomedical Signal Processing System Operating at Near-Threshold", IEEE Transactions on Biomedical Circuits and Systems, vol. 5, No. 6, pp. 546-554, (Dec. 2011).

* cited by examiner

400

| | A first prior art | A second prior art | A third prior art | The present embodiments | |
|---|---|---|---|---|---|
| Scale | 3 dB BW (Hz) | 3 dB BW (Hz) | 3 dB BW (Hz) | 3 dB BW (Hz) | 3 dB BW (Hz) |
| Fs | 250 | 250 | 300 | 500 | 250 |
| 1 | 62.5~125 | 62.5~125 | 75~150 | 125~250 | 62.5~125 |
| 2 | 18~58.5 | 18~58.5 | 21.6~70.2 | 62.5~125 | 18~58.5 |
| 3 | 8~27 | 8~27 | 9.6~32.4 | 18~58.5 | 8~27 |
| 4 | 4~13.5 | 4~13.5 | 4.8~16.2 | 8~27 | 4~13.5 |
| 5 | 2~6.5 | 2~6.5 | 2.4~7.8 | 4~13.5 | 2~6.5 |
| 6 | 1~3.25 | 1~3.25 | 1.2~3.9 | 2~6.5 | 1~3.25 |
| QRS | S1~S4 | S1~S4 | S3 | S4 | — |
| P/T | S4 | S4 | — | — | S4 |

*FIG. 4*

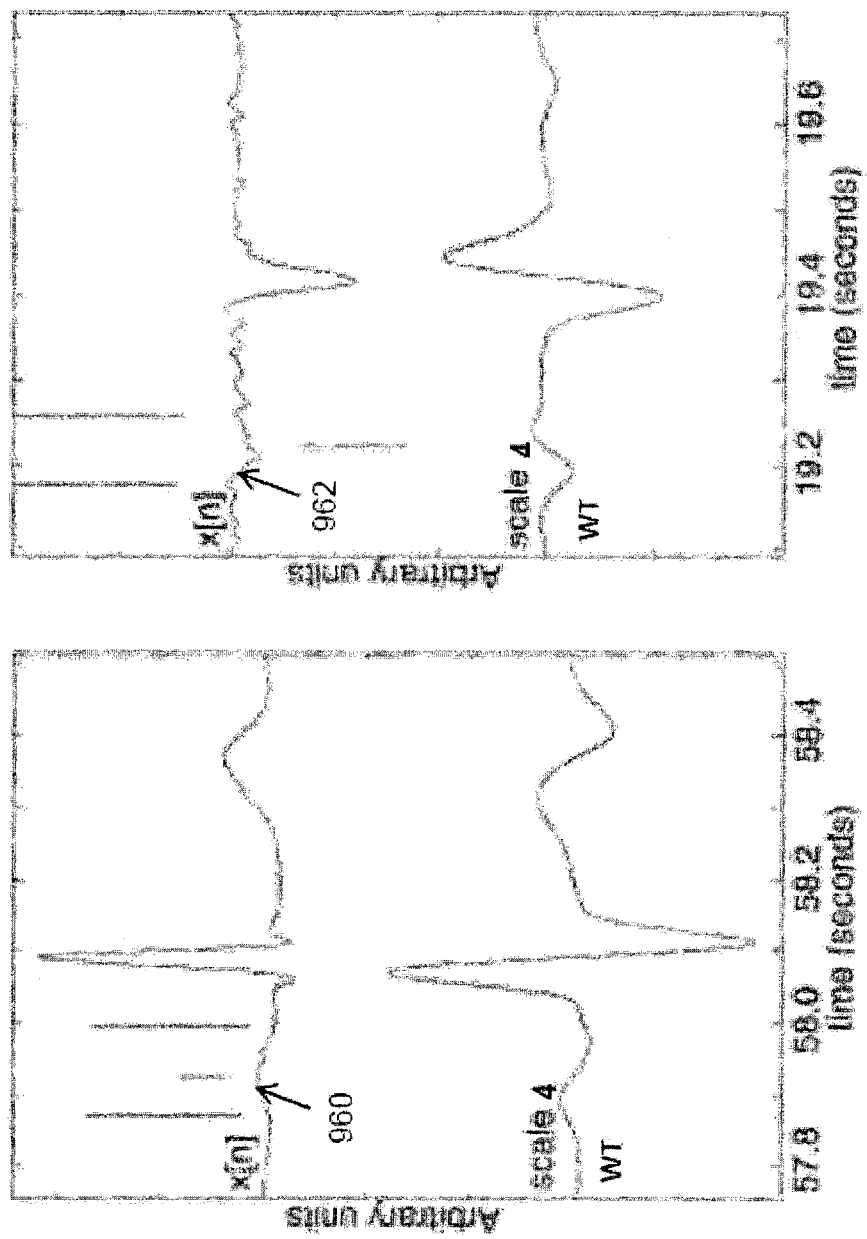

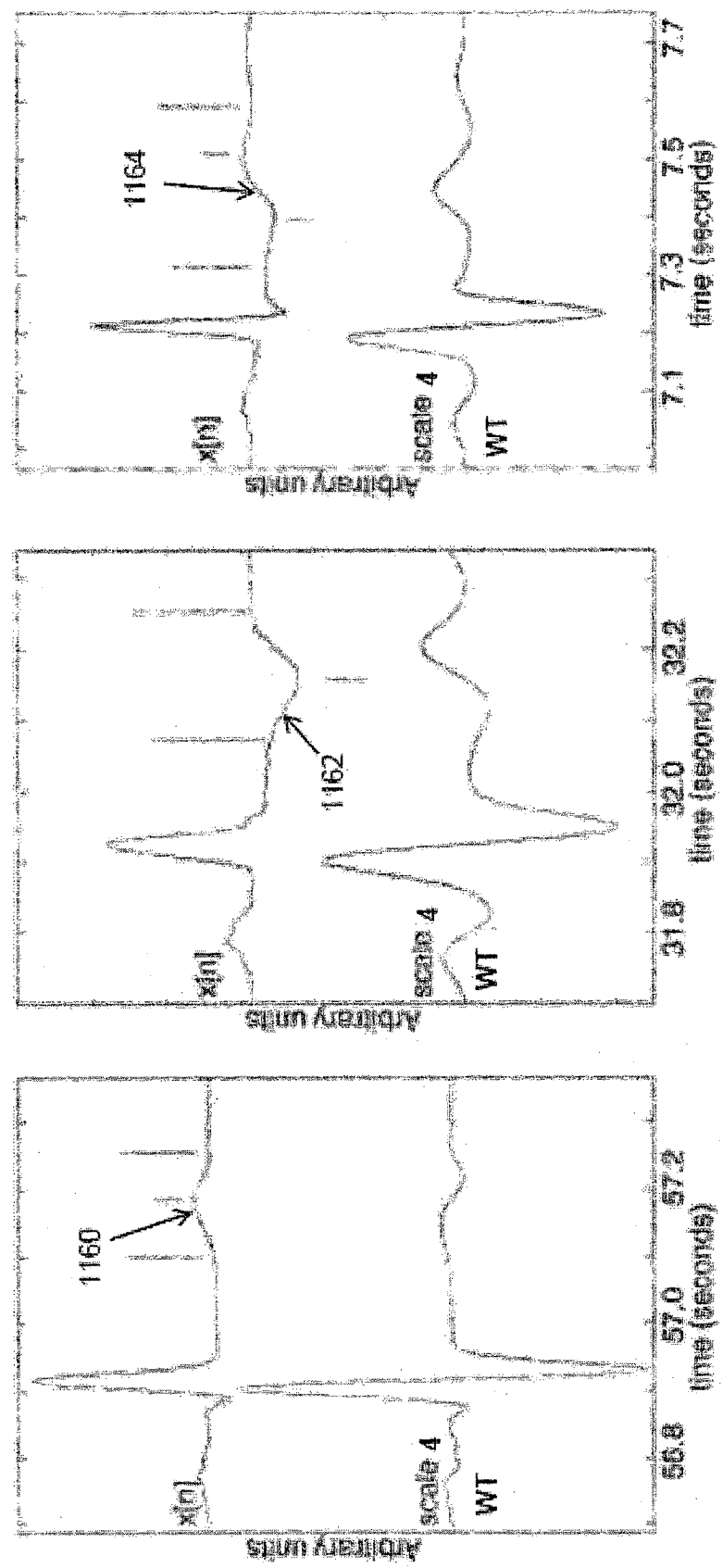

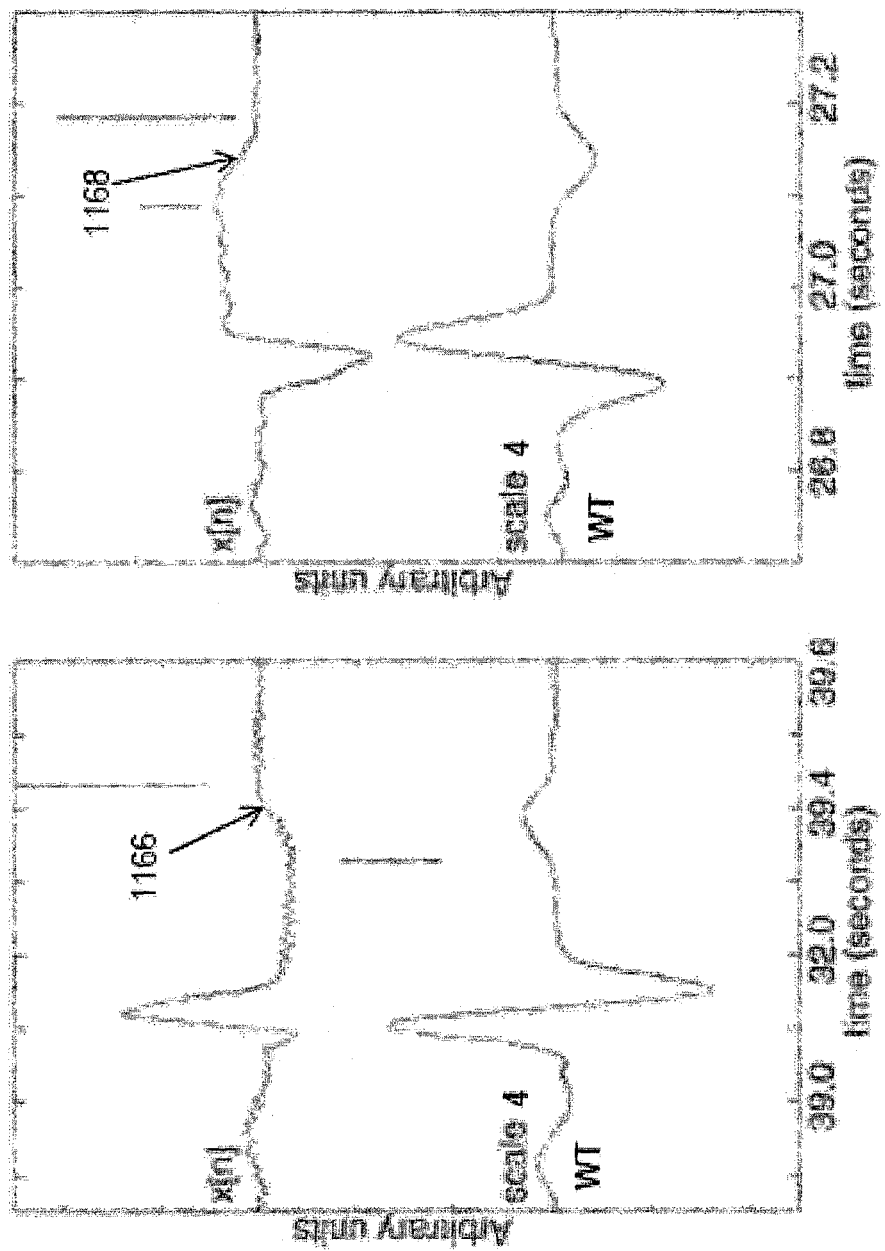

REAL-TIME MULTI-FUNCTIONAL ECG SIGNAL PROCESSING SYSTEM, DSPE FOR THE ECG SIGNAL PROCESSING SYSTEM, AND METHOD THEREOF

CROSS-REFERENCE TO RELATED APPLICATIONS

The present application is a U.S. National Phase Application under 35 U.S.C. §371 of International Application No. PCT/SG2014/000276, filed on 12 Jun. 2014, entitled REAL-TIME MULTI-FUNCTIONAL ECG SIGNAL PROCESSING SYSTEM, DSPE FOR THE ECG SIGNAL PROCESSING SYSTEM, AND METHOD THEREOF, which claims priority to Singaporean Patent Application No. 201304531-5, filed on 12 Jun. 2013.

FIELD OF THE INVENTION

The present invention generally relates to electrocardiogram (ECG) signal processing systems, and more particularly relates to an electrocardiogram (ECG) signal processing system for use in long-term cardiac status monitoring and classification, and/or remote and/or on-chip cardiac monitoring and comprehensive diagnosis.

BACKGROUND

Electrocardiogram (ECG) is a common medical investigation technique, which is widely used in all healthcare for diagnosis and monitoring of numerous conditions from heart attacks to electrolyte imbalances.

Long term ambulatory ECG monitoring is highly desired to detect, characterize and document cardiac arrhythmias in clinical practice. It can also detect periods when a user's heart is suffering from the effects of inadequate blood supply or myocardial ischaemia. Several customized digital ECG signal processors have been developed. However, many of these mainly focus on the heart beat rate (HBR) calculation which is basically based on the R-R interval information retrieved from QRS peak detections.

For clinical treatment, information on QRS peak detection is not sufficient for comprehensive diagnosis. Clinical professionals also require other important features related to P and T waves, as well as noise filtering and clean ECG reconstruction. Some conventional devices have realized more comprehensive functions. For example, a multiple functional ECG signal processing for wearable applications of long-term cardiac monitoring has been proposed by X. Liu et al, as published on IEEE Trans. Biomed. Eng., vol. 58, no. 2, pp. 380-389, January 2011, which can perform noise suppression and baseline drifting removal to generate clean ECG waveforms. However, due to the increasing complexity in the signal processing algorithms, the consumptions on power and silicon areas are comparatively high for hardware implementation.

Thus, there is a need in the art for a robust ECG processing system which is able to provide clean ECG signal output with enhanced energy and area efficiency and reduced signal processing power consumption.

Further, there is also a need in the art for the robust ECG processing system to be able to analyse comprehensive cardiac features, which include not only the QRS peak complex, but also P waves and T waves.

SUMMARY

According to a first aspect of the present invention, there is provided an electrocardiogram (ECG) signal processing system, the ECG signal processing system comprising an analog-to-digital converter (ADC) configured to convert an input analog ECG signal into a digital ECG signal; a digital signal processing engine (DSPE) coupled to the ADC to receive the digital ECG signal, the DSPE being configured to decompose and reconstruct the digital ECG signal; and a dynamic system clock source coupled to the ADC and the DSPE for dynamic signal sampling, the dynamic system clock source clocking the ADC and the DSPE at a first frequency $f_1$ to detect one or more first parameters of the input analog ECG signal and at a second frequency $f_2$ to detect one or more second parameters of the input analog ECG signal.

According to a second aspect of the present invention, there is provided a digital signal processing engine (DSPE) for electrocardiogram (ECG) signal processing, the digital signal processing engine (DSPE) being coupled to a digital ECG signal input and comprising: a wavelet transformation (WT) unit, the WT unit comprising a plurality of scales; wherein the WT unit is adapted to decompose the digital ECG signal into a plurality of wavelets, each wavelet being output from one of the scales; and a plurality of signal processing blocks, each of the signal processing blocks coupled to one or more outputs of the scales and configured to receive and process the one or more wavelets from the respective outputs, wherein the signal processing blocks provide processing functions which differ from one another; wherein the WT unit and the plurality of signal processing blocks are coupled to a dynamic system clock source for dynamic signal sampling, the dynamic system clock source clocking the DSPE at a first frequency $f_1$ to detect one or more first parameters of the input digital ECG signal and at a second frequency $f_2$ to detect one or more second parameters of the input digital ECG signal.

According to a third aspect of the present invention, there is provided a method for processing an electrocardiogram (ECG) signal, the method comprising: providing a first device configured to convert an input ECG analog signal into a ECG digital signal; providing a second device coupled to the first device to receive the digital ECG signal, the second device being configured to decompose and reconstruct the digital ECG signal; and providing a dynamic clock source connected to the first and the second device, wherein the dynamic clock source clocking the first and the second device at a first frequency $f_1$ to detect one or more first parameters of the input analog ECG signal and at a second frequency $f_2$ to detect one or more second parameters of the input analog ECG signal.

BRIEF DESCRIPTION OF DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 4 depicts a table that lists 3 dB WT bandwidths (and their respectively corresponding scales) of ECG signal characteristics, i.e., QRS complex and P/T waves, at different sampling frequencies in accordance with the present embodiments and conventional ECG processing systems.

FIGS. 9B-9C depict morphologies of P wave, including positive P wave (P+) and negative P wave (P−), in accordance with the present embodiments.

FIGS. 11B-11F depict morphologies of T wave, including upwards T wave, downwards T wave, positive T wave (T+), negative T wave (T−), and biphasic T wave (T+/−, T−/+), in accordance with the present embodiments.

Skilled artisans will appreciate that elements in the figures are illustrated for simplicity and clarity and have not necessarily been depicted to scale. For example, the dimensions of some of the elements in the block diagrams or flowcharts may be exaggerated in respect to other elements to help to improve understanding of the present embodiments.

DETAILED DESCRIPTION

The following detailed description is merely exemplary in nature and is not intended to limit the invention or the application and uses of the invention. Furthermore, there is no intention to be bound by any theory presented in the preceding background of the present invention or the following detailed description. It is an intent of the present embodiment to present a novel real-time multi-functional ECG processing system, whose architecture is herein proven to achieve high energy and area efficiency. Several novel embodiments are provided to achieve high energy efficiency and satisfying performance of on-chip ECG/cardiac analysis and diagnosis. An adaptive system operation clocking is provided for the overall system, including both ADC and digital signal processing module, for example, the digital signal processing engine (DSPE). Pseudo-downsampling WT & IWT and adaptive storing are also provided to achieve lower computational power and required storage units. Further, run-length compression with noise suppression is proposed to further reduce the required number of storage units without significant information distortion. Lastly, on-chip low-complexity signal processing schemes are provided to perform more critical cardiac feature extractions, benefiting long-term cardiac monitoring and clinical treatment, the cardiac feature extractions in accordance with the present embodiment comprising QRS complex, P waves and T waves.

Figure 1:
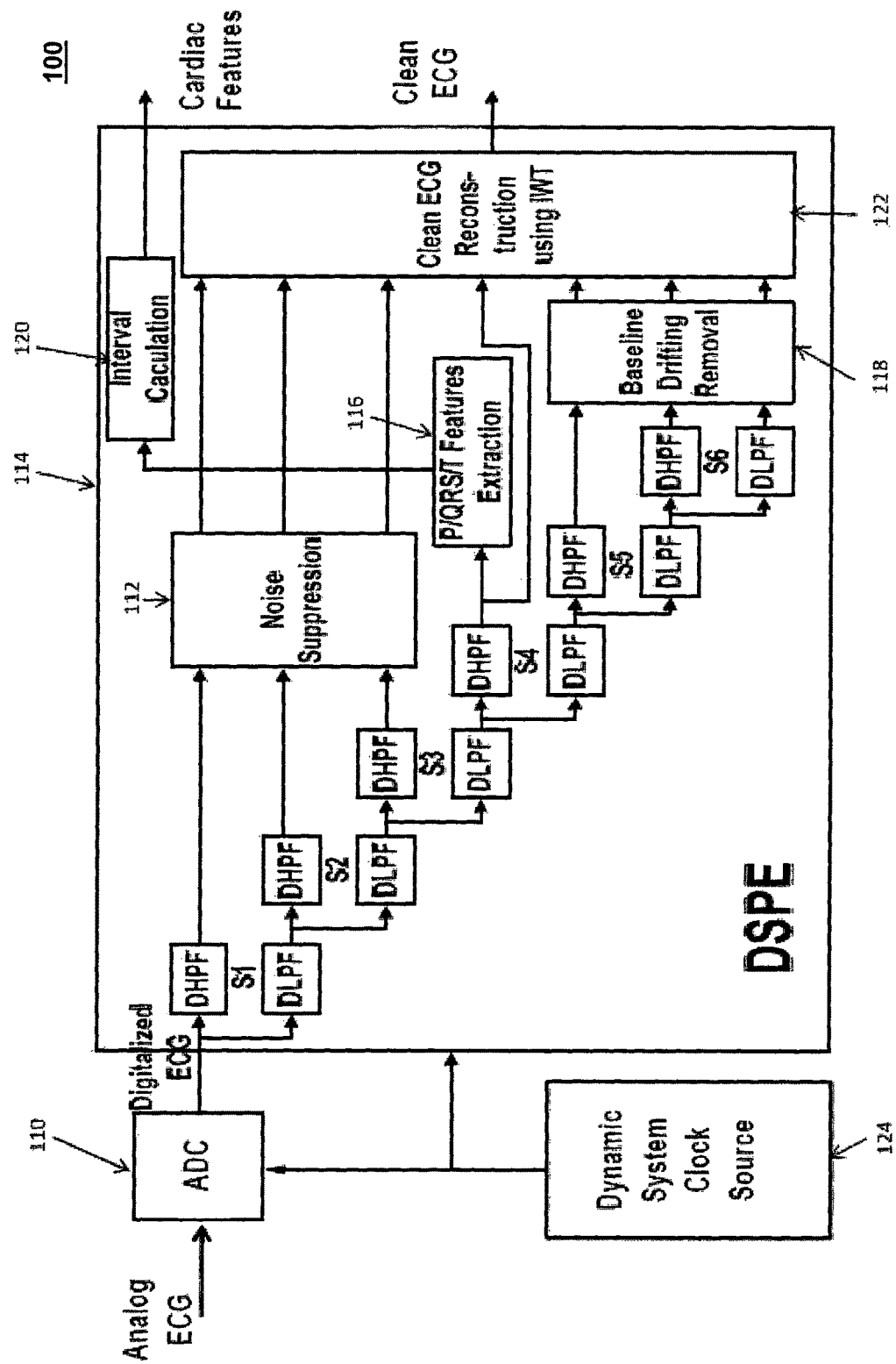
FIG. 1 depicts a block diagram of an electrocardiogram (ECG) signal processing system comprising an analog-to-digital converter (ADC), a digital signal processing engine (DSPE) and a dynamic system clock source coupled to both the ADC and the DSPE in accordance with a present embodiment.

Referring to FIG. 1, a block diagram 100 of an ECG signal processing system in accordance with a present embodiment is depicted.

An analog-to-digital converter (ADC) 110 and a digital signal processing engine (DSPE) 114 are illustrated in the ECG signal processing system. The ADC 110 acquires analog ECG signals and converts the acquired analog ECG signals into the digital domain, which subsequently flows into the DSPE 114. The DSPE decomposes the digitized ECG signals through a plurality of decomposition high pass filters (DHPFs) and decomposition low pass filters (DLPFs), such that the digitized ECG signals turn into a plurality of filter bank scales. The outputs of these DHPFs and DLPFs converge at a signal processing block, for example, a clean ECG reconstruction block 122, to reconstruct/synthesise clean ECG signals. Preferably, prior to the clean ECG construction block 122, at least a noise suppression block 112 and at least a baseline drifting removal block 118 are coupled to the outputs of the DHPFs and DLPFs, so as to conduct high frequency noise suppression and artificial baseline drift removal to the outputs.

In the present embodiment as shown in FIG. 1, a P/QRS/T features extraction block 116 is proposed to perform important cardiac features extraction. The P/QRS/T features extraction block 116 is preferably coupled to at least one output of the plurality of the DHPFs and DLPFs. An interval calculation block 120 is also provided to receive and calculate the signals streaming from the P/QRS/T features extraction block 116, and then output the indicators of P/QRS/T waves, which will be shown in FIG. 15.

A dynamic system clock source 124 is connected to both the ADC 110 and the DSPE 114, as shown in FIG. 1, to control the ECG signal processing system to sample at dynamic system frequencies. The dynamic system clock source 124 switches between different frequencies with certain duty cycles, depending on the required temporal resolutions. According to the characteristics of ECG signals, the present embodiment applies 500 Hz as the maximum sampling rate and 250 Hz as the minimum sampling rate.

Quadratic spline wavelet transform (WT) is conventionally used and presently adopted in the present embodiment for signal decomposition and reconstruction. Four types of WT filters are used to decompose the ECG signals as a plurality of wavelets or to reconstruct the wavelets back into ECG signals. That is, decomposition high pass filter (DHPF) and decomposition low pass filter (DLPF) as described above, reconstruction high pass filter (RHPF), and reconstruction low pass filter (RLPF) (RHPF and PLPF are not shown in FIG. 1). Six pairs of DHPF and DLPF are employed, as shown in FIG. 1, to obtain six scales WT in accordance with the present embodiment. As shown in FIG. 1, the DHPF outputs of lower scales, for example, the first to the fourth scales, are preferably used for noise suppression and cardiac features extraction. Preferably, the DHPF outputs of the middle scales, for example, the fourth scale, are used for cardiac features (P/QRS/T) extraction. On the other hand, the DHPF and DLPF outputs of higher scales, for example, the fifth to the sixth scales, are preferably adopted for baseline drifting removal.

As shown in FIG. 1, the ECG signal processing system outputs extracted cardiac features from interval calculation block 120 and reconstructed clean ECG waveforms from clean ECG reconstruction block 122.

Figure 2:
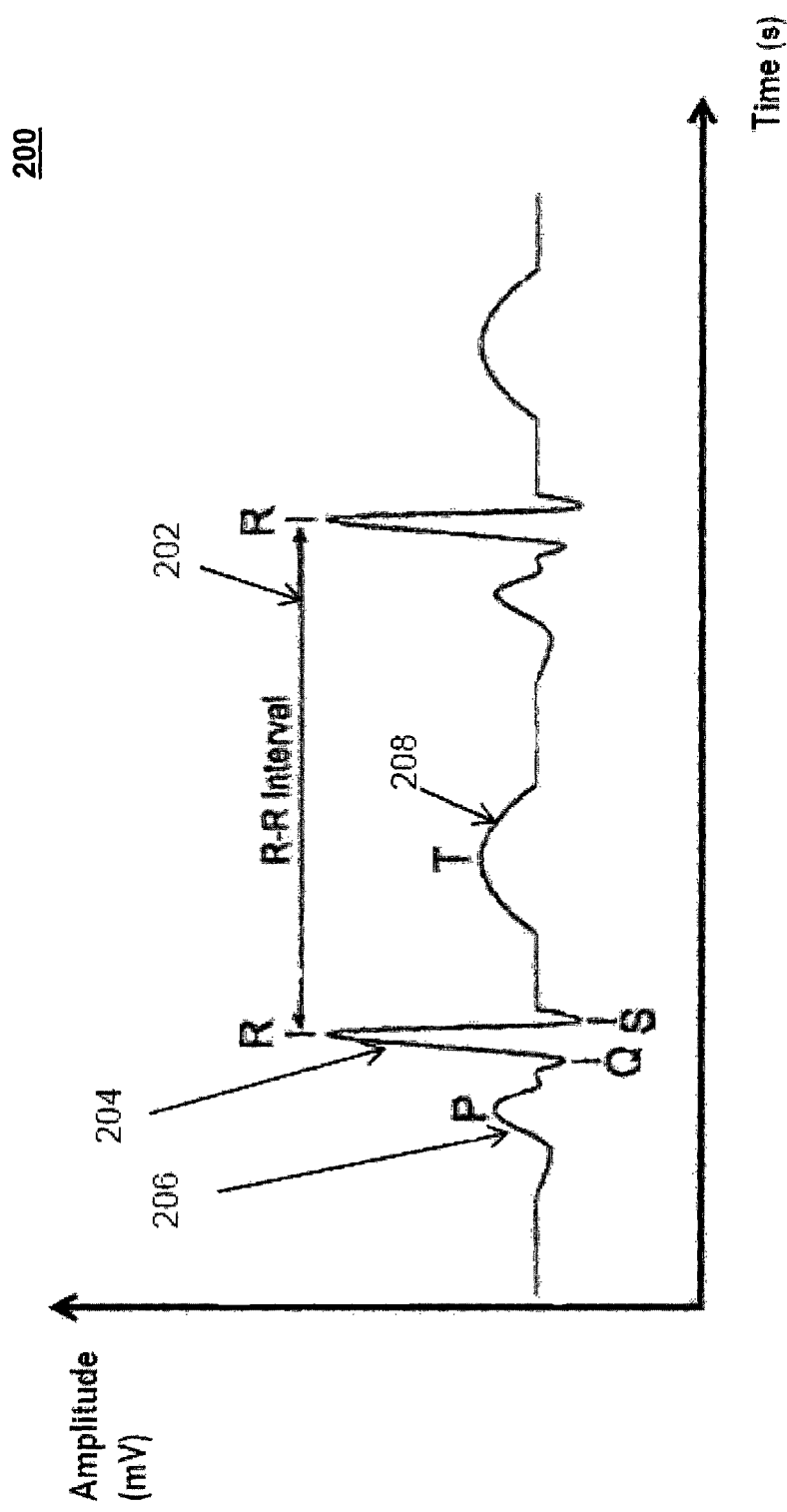
FIG. 2 depicts a graph of the morphology of an ECG wave.

Referring to FIG. 2, a graph 200 illustrates the morphology of ECG waveforms, with a single ECG waveform shown in the R-R interval 202. As shown in FIG. 2, the most significant characteristics of an ECG waveform, are the QRS complex 204, the P wave 206 and the T wave 208. In the frequency domain, theoretically, the bandwidth of QRS complex, P wave, and T wave are around 10-60 Hz, 4-15 Hz, and 4-15 Hz, respectively. Conventional ECG signal processing uses constant sampling rates/frequencies which satisfy the Nyquist sampling theorem for a QRS complex for sampling ECG waveforms. Such constant operation frequency has also been adopted for both ADC and DSPE. However, a person skilled in the art would observe that the QRS complex requires a higher sampling rate with a low duty cycle around 23%, while P and T waves require a lower sampling rate with a higher duty cycle. Hence it is not necessary and considerably power-wasting to apply high frequency on P wave and T wave samplings (i.e., the same as that used on QRS complex sampling).

Figure 3:
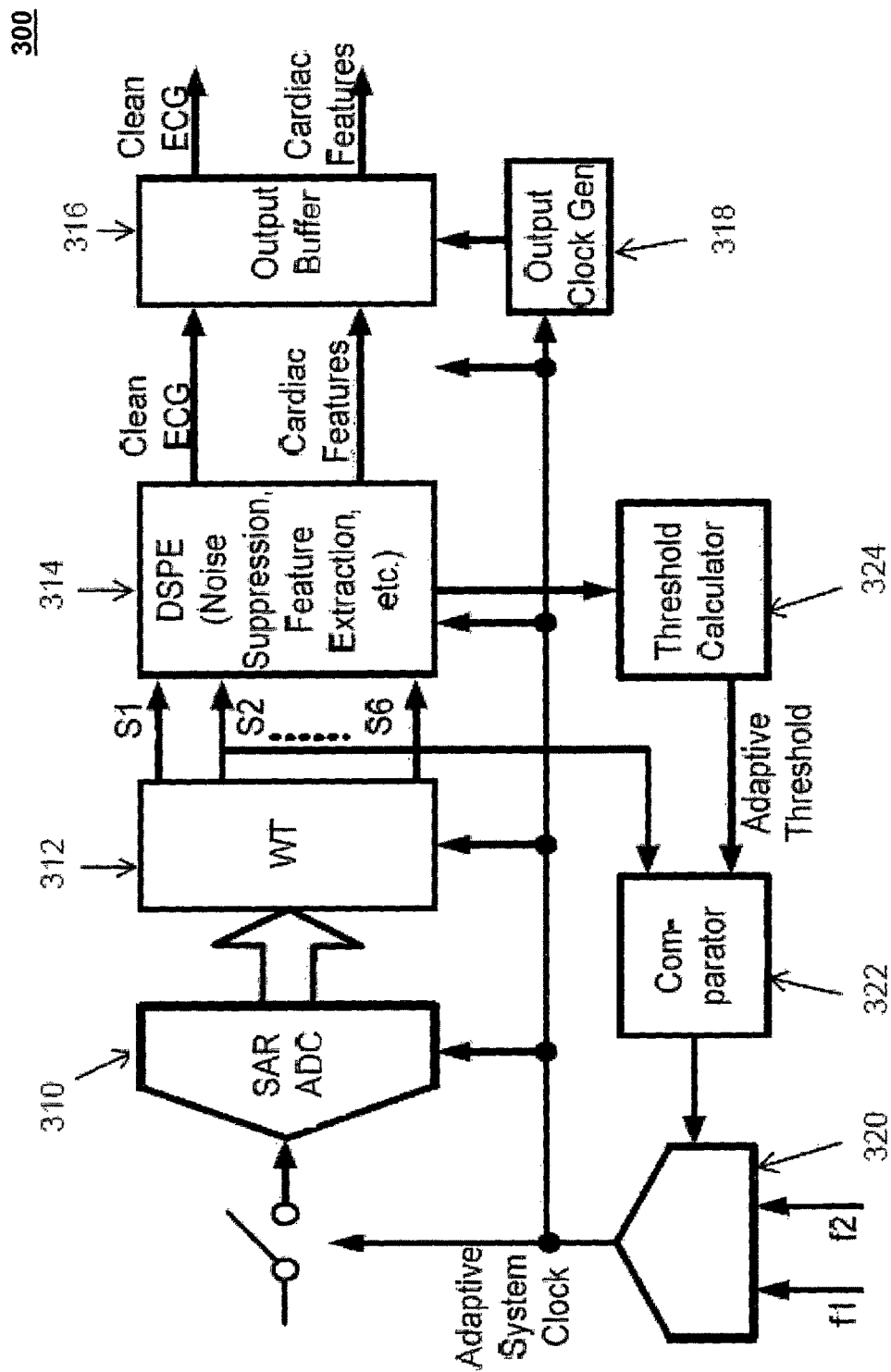
FIG. 3 depicts a block diagram illustrating the adaptive operation clocking in accordance with a variation of the present embodiment.

Referring to FIG. 3, a novel adaptive system clock is provided in accordance with a variation of the present embodiment. FIG. 3' depicts a block diagram 300 illustrating an ECG signal processing system which comprises the adaptive operation clocking in accordance with the variation of the present embodiment.

Similar to the ADC 110 of FIG. 1, an ADC 310 is provided to receive analog ECG signals and convert them into digital ECG signals. The ADC 310 is preferably a successive approximation (SAR) for low power consumption and low design complexity. The digitalized ECG signals flow into a wavelet transformation (WT) unit 312 which sequentially decomposes the ECG signals into a plurality of wavelet scales. In the present embodiment as shown in FIG. 3, the WT unit decomposes the digitalized ECG signals into 6 cascaded wavelet scales and outputs the 6 cascaded wavelet scales into a DSPE 314. The DSPE 314 comprises at least a clean ECG reconstruction block, a noise suppression block and a cardiac feature extraction block, and outputs clean ECG signals and cardiac features. At the output of the DSPE 314, an output buffer 316 is provided to synchronize the DSPE output at a re-sampling rate provided by an output clock generator 318 that is derived from the adaptive system clock (which will be discussed in the following description), to obtain the correct clean ECG waveform and extracted features in the time domain. It is understood by a skilled person in the art that the use of the output buffer 316 could be omitted in various embodiments.

A multiplexer 320 is introduced into the present embodiment shown in FIG. 3 to provide the adaptive system clock by way of switching between a first frequency f1 and a second frequency f2. In the present embodiment, f1 is a high frequency while f2 is a low frequency. The output of the multiplexer 320 is utilized for the overall system, including the sub-modules in ADC 310 and DSPE 314. The multiplexer 320 is controlled by a comparator 322 comparing inputs between the DHPF output of Scale 2 (DHPF_S2) and an adaptive threshold value THf from a threshold calculator 324. If the value of DHPF_S2 is larger than THf, the system operates at the fast frequency f1, to perform QRS related signal processing. After a certain pre-defined period, the system operation frequency goes back to the low frequency f2. The adaptive threshold value THf is calculated by the threshold calculator 324 from the noise suppression module of the DSPE 314.

Some ADC architectures with adaptive sampling rate or adaptive resolution may have been used in the state of the art. For example, one adaptive sampling ADC has been utilized for ECG signal acquisition. Such conventional adaptive samplings are basically to provide an analog circuit module to sense the rate of change of the input signals by using a switched capacitor (SC) differentiator, and compare the rate with a threshold voltage to select different sampling rates. However, since the differentiator amplifies high frequency components, the outputs of the comparator have a higher chance to be deteriorated by high frequency interference. In contrast, in accordance with the present embodiment, it is DHPF_S2 that is used as the comparator input. By doing so, high frequency interference is greatly reduced as most of such interference falls in DHPF_S1.

Meanwhile, DHPF_S2 also has less influence of artificial baseline drifting as most of such drifting take place in higher scales, such as Scales 5-6. The conventional switched capacitor structure consumes a comparatively larger area, especially for low frequency signals (e.g., ECG signals). However, since the WT 312 and comparator 322 of the present embodiment are implemented in the digital domain, and the DHPF outputs are inherently utilized for the further digital signal processing (e.g., noise suppression, QRS detection, etc.), there is almost no significant area and power consumption overhead in the ECG processing systems in accordance with the present embodiments. In addition, another issue presented by conventional adaptive sampling is that the comparator and threshold generation modules are designed in the analog domain which has higher chance to be disturbed by different types of noise and interference. Such drawbacks of the prior art are also overcome by the digital solution of the present embodiments.

If the adaptive clocking is applied for the ADC only whereas the DSPE maintains constant clocking, the power consumption of the overall system cannot be significantly reduced. In the present embodiments, as shown in FIGS. 1 and 3, the adaptive operation clocking is applied to the complete ECG processing system, including both ADC 110, 310 and DSPE 114, 314.

Referring to FIG. 4, a table 400 is depicted that lists 3 dB WT bandwidths (and their respectively corresponding scales) of ECG signal characteristics, i.e., QRS complex and P/T waves, at different sampling frequencies in the present embodiments and conventional ECG processing systems. As the important cardiac features that the present embodiments target to extract include QRS complex, P wave and T wave, with reference to FIG. 4 showing their corresponding WT bandwidth, it can be observed that if the sampling rate is 500 Hz, the dominant components of QRS peak will fall at Scale 4. If the sampling rate is 250 Hz, the dominant components of P and T waves will also fall at Scale 4. Therefore, in the present embodiments, according to the comparator's output, the system operation frequency is configured to switch between 500 Hz and 250 Hz. The high frequency f1, 500 Hz, is adopted to detect QRS related characteristics and associated features; whereas the low frequency f2, 250 Hz, is adopted for P and T waves related characteristics identification and features extraction. Since the cardiac duty cycle of the QRS complex is approximately 23%, by using the provided dynamic system clocking, the power consumption of the overall system can be significantly reduced by around 38%, compared to conventional systems.

Non-downsampling WT (NDWT) is conventionally selected for ECG signal decomposition and reconstruction, as it prevails downsampling WT (DWT) that makes the signal representation time-variant and reduces the temporal resolution of the wavelet coefficients with scales increasing. However, the NDWT has a major shortcoming—huge data storage requirements.

According to the NDWT, in the decomposition part, $l_{D,j}(k)$ and $h_{D,j}(k)$ are denoted as the coefficients of DLPF and DHPF of scale $j$. For scale 1, $l_{D,1}(k)$ and $h_{D,1}(k)$ are expressed by the following Equations 1 and 2, $$l_{D,1}(k)=(1/8)\cdot\{\delta(k+2)+3\delta(k+1)+3\delta(k)+\delta(k-1)\} \tag{1}$$

$$h_{D,1}(k)=2\{\delta(k+1)-\delta(k)\} \tag{2}$$

respectively. For scales j>1, $l_{D,j}(k)$ and $h_{D,j}(k)$ are obtained by inserting $2^{j-1}-1$ zeros between each of the coefficients of $l_{D,1}(k)$ and $h_{D,1}(k)$.

In the reconstruction part, $l_{R,j}(k)$ and $h_{R,j}(k)$ are denoted as coefficients of RLPF and RHPF of scale j, respectively. For scale 1, $l_{R,1}(k)$ and $h_{R,1}(k)$ are expressed by the following Equations 3 and 4, $$l_{R,1}(k)=(1/8)\cdot\{\delta(k+2)+3\delta(k+1)+3\delta(k)+\delta(k-1)\} \tag{3}$$

$$h_{R,1}(k)=-0.0078125\delta(k+2)-0.0546875\delta(k+1)-0.171875\delta(k)+0.171875\delta(k-1)+0.0546875\delta(k-2)+0.0078125\delta(k-3) \tag{4}$$

respectively. For scales j>1, $l_{R,j}(k)$ and $h_{R,j}(k)$ are obtained by inserting $2^{j-1}-1$ zeros between each of the coefficients of $l_{R,1}(k)$ and $h_{R,1}(k)$.

From Equations 1-4, it can be observed that there are a huge number of delays in ECG decomposition, especially for higher scale NDWT. Considering the ECG reconstruction, there is also a huge number of processing delays' for different scales that need to be synchronized before they are fed into the reconstruction block. For example, the total storage units required for 8 scales NDWT based decomposition and reconstruction is around 140 k bits. This huge number of storage units results in significant power and area consumption.

Figure 5:
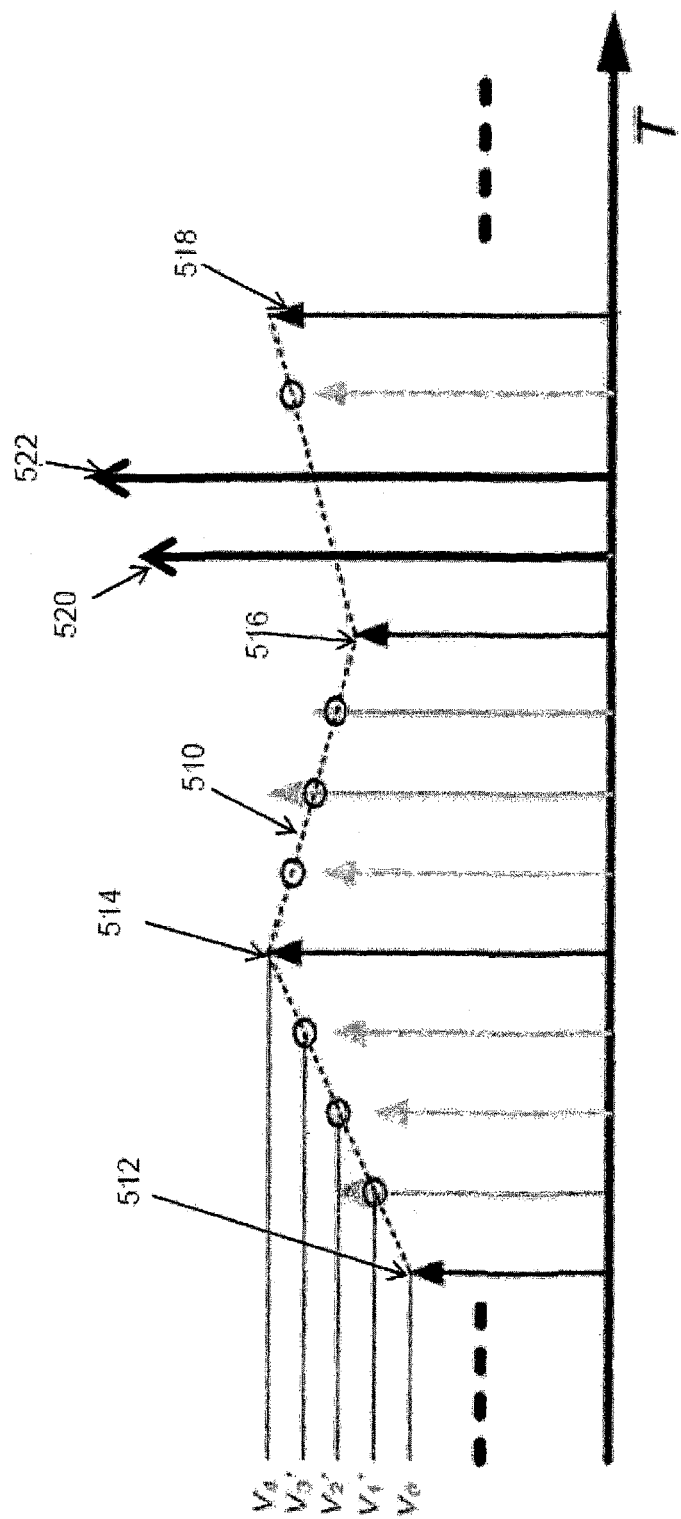
FIG. 5 depicts a graph illustrating an exemplary sample of Pseudo-downsampling wavelet transformation (WT) at Scale 3 in accordance with the present embodiments.

In order to reduce the required storage size, a novel pseudo-downsampling WT (PDWT) and pseudo-upsampling WT (PUWT) scheme is provided in accordance with the present embodiments. Referring to FIG. 5, an exemplary graph 500 of Pseudo-downsampling wavelet transformation (WT) at Scale 3 is depicted in accordance with the present embodiments is depicted.

In the provided PDWT and PUWT scheme, $x_j(i)$ and $y_j(i)$ are denoted as outputs of DHPF of Scale j (DHPF_Sj) and DLPF of Scale j (DLPF_Sj), respectively. Conventionally, all $x_j(i)$ and $y_j(i)$ need to be stored. In the provided PDWT and PUWT scheme, similar as downsampling WT, DHPF and DLPF outputs in every $2^{j-1}-1$ samples will firstly be stored. As shown in FIG. 5, $y_3(0)$ 512, $y_3(4)$ 514, $y_3(8)$ 516, $y_3(12)$ 518 . . . will be stored in storage units. The storage units could be shift-registers or SRAMs.

Besides DHPF and DLPF outputs in every $2^{j-1}-1$ samples, an average increment $\Delta y_j(k)$ between $y_j(i)$ and $y_j(i+2^{j-1})$ will also be calculated and stored in storage units. The average increment $\Delta y_j(k)$ is expressed by the following Equation 5:

$$\Delta y_j(k)=[y_j((k+1)*2^{j-1})-y_j(k*2^{j-1})]/2^{j-1} \tag{5}$$

where k=0, 1, 2, . . . . Therefore, the DHPF outputs between $y_j(k*2^{j-1})$ can be approximated by interpolating the average increment $\Delta y_j(k)$, as expressed by the following Equation 6:

$$y_j(k*2^{j-1}+n)=y_j(k)+n*\Delta y_j(k) \tag{6}$$

where n=1, 2, . . . , $2^{j-1}-1$. By virtue of the PDWT and PUWT scheme, the required storage units can be significantly reduced, as only $y_j(k*2^{j-1})$ and $\Delta y_j(k)$ need to be stored. For example, operation in accordance with the present embodiment can reduce the number of storage units for Scale 6 by approximately 95%, as compared with NDWT. In addition, issues of time-variant in DWT can also be eliminated under this scheme.

However, under the PDWT and PUWT scheme, there might be distortions on NDWT outputs, because the wavelet DHPF and DLPF outputs between $y_j(k*2^{j-1})$ are only approximately obtained. To alleviate the distortion, a compensation mechanism is also proposed in accordance with the present embodiment. In the compensation mechanism, the actual, values of $y_j(k*2^{j-1}+n)$ are compared with a pre-defined threshold $T_d$ 510:

$$T_d=\alpha\times y_j(k*2^{j-1}+n) \tag{7}$$

where $\alpha$ is a comparison factor. If the absolute value of $y_j(k*2^{j-1}+n)$ is smaller than the absolute value of $T_d$, Equation 6 will be used to approximate $y_j(k*2^{j-1}+n)$; otherwise the actual value of $y_j(k*2^{j-1}+n)$ will be saved in the storage units and will be used for the further processing.

For example, as shown in FIG. 5, two significant actual values SAV1 520 and SAV2 522 are depicted to represent PDWT outputs which exceed $T_d$ 510, and thus only these 2 PDWT outputs SAV1 and SAV2 will be stored along with $y_j(k*2^{j-1})$, for example, $y_3(0)$ 512, $y_3(4)$ 514, $y_3(8)$ 516, $y_3(12)$ 518, in the storage units; whereas other PDWT outputs will be approximated by Equation 6.

In view of the above description, under the PDWT and PUWT scheme, the significant wavelet coefficients, such as SAV1 520 and SAV2 522 illustrated in FIG. 5, can be maintained for further signal processing. Thus, the distortions on PDWT can be improved with a reduced amount of additional storage. For the lower scales of NDWT, because the value of $2^{j-1}-1$ is not so large, the required number of storage units is accordingly also not so large, thus the provided PDWT may seem less necessary, so that can be omitted in various embodiments. However, for higher scales, the value of $2^{j-1}-1$ becomes significant, thus the provided PDWT becomes more desired. Since the DLPF and DHPF outputs of higher scales correspond to lower frequency signal components, the number of significant wavelet outputs is comparatively small, and thus the required additional storage units is comparatively low. The number of additional storage units depends on the value of $\alpha$. The proposed PDWT can be adopted for both the delays in FIR filtering and the synchronization delays between DHPF and RHPF. For hardware implementation, total required storage can be reduced by 40%, based on the present experiments that deploy 6 scales WT for decomposition and reconstruction and use 16 bits inputs and outputs for WT of each scale.

Figure 6:
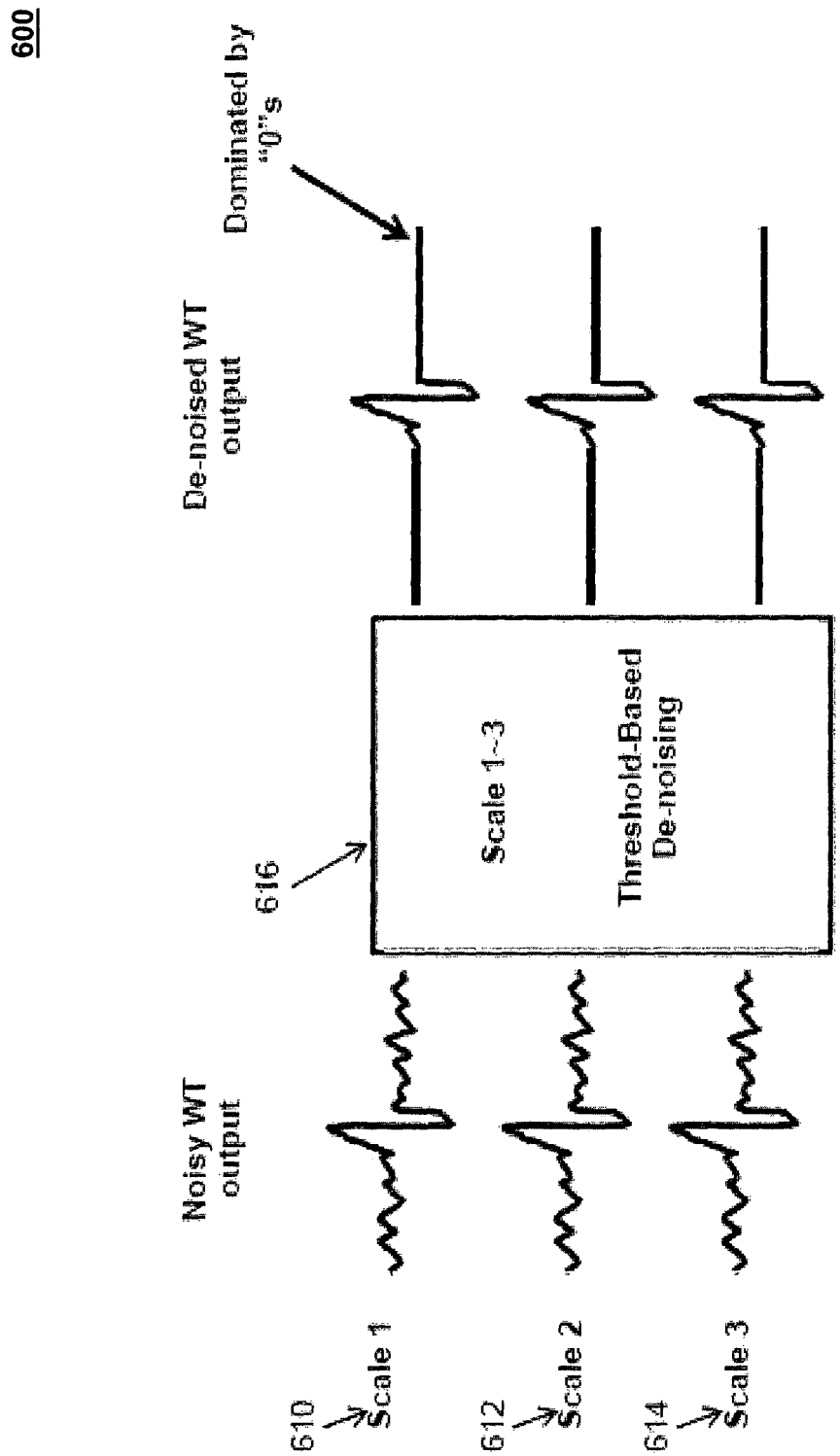
FIG. 6 depicts a graph illustrating adaptive threshold-based noise suppression for Scales 1-3 in accordance with the present embodiments.

Referring to FIG. 6, a graph 600 illustrating adaptive threshold-based noise suppression as shown in FIG. 1 for Scale 1 610, Scale 2 612 and Scale 3 614 in accordance with the present embodiments, is depicted. Under the adaptive threshold-based noise suppression 616, the DHPF outputs smaller than an adaptive threshold is basically forced to zero. Therefore, after noise suppression, the DHPF outputs of Scales 1-3 will comprise dominated portions of zeros and only small portions of continuous non-zero values, as shown in FIG. 6. Inspired by this fact, a run-length data compression scheme is herein provided to cooperate with adaptive threshold-based noise suppression, without further information distortion.

Figure 7:
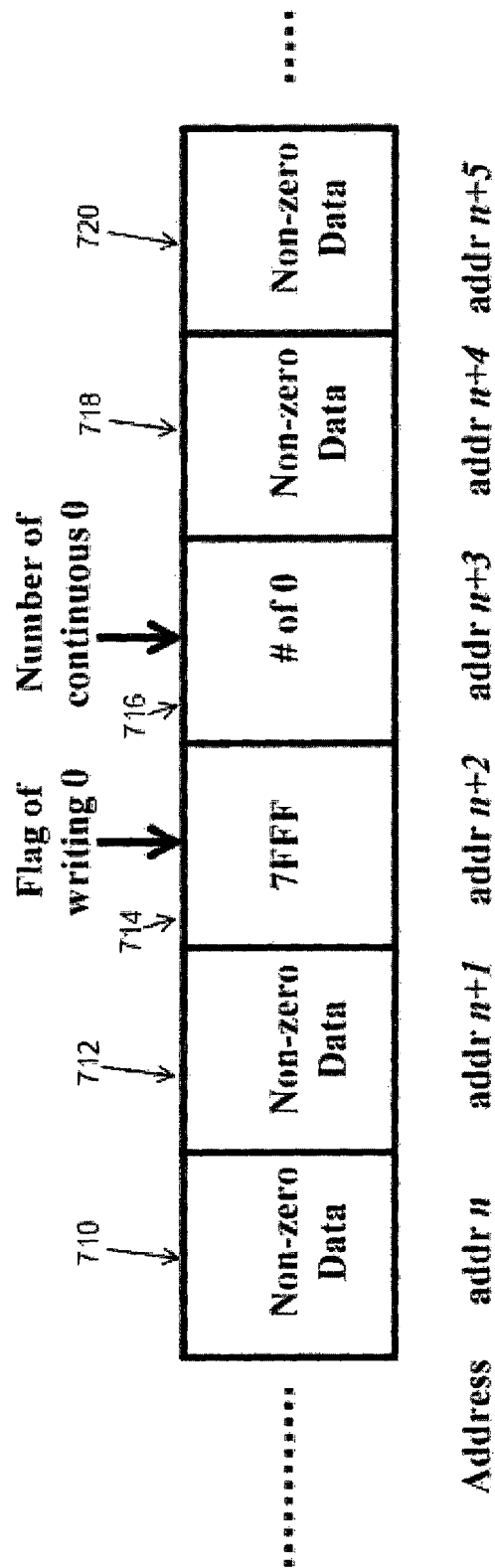
FIG. 7 depicts a data storage structure configured to realize run-length data compression, preferably for Scales 1-3, in accordance with the present embodiments.

Referring to FIG. 7, a data storage structure 700 is depicted to implement the run-length data compression, preferably for Scales 1-3, in accordance with the present embodiments. The non-zero data will be stored in the storage units, for example in address n 710, n+1 712, n+4 718 and n+5 720. Once continuous zeroes are detected, a flag of writing 0 will be written into storage units, for example in address n+2 714. Following that, a counter starts to count the number of zeros. Only after detecting the next non-zero data, the counted number of zeros is written into storage units, in for example address n+3 716, followed by the next non-zero data stored in address n+4 718. Accordingly, at the input side of RHPF, once the flag of writing 0 is red out, the continuous "0" s will be fed into RHPF according to the detected number of continuous zeroes. Under the run-length data compression scheme, data compression is naturally combined with the threshold-based noise suppression to further reduce the required number of storage units for synchronization delays. Further, there is no further information distortion on top of noise suppression.

To reduce workloads of medical professionals and to save power consumption of ECG device, it is highly recommended that the ECG recording system is equipped with comprehensive on-chip cardiac analysis and diagnosis capabilities. Many papers have already introduced the ECG signal processing techniques, and some of them have discussed the on-chip signal processing. These existing on-chip ECG signal processing methods mainly focus on feature extractions of QRS peaks to derive the heart beat rate (HBR). However, for clinical diagnosis and treatment, information on QRS peak detection alone is not sufficient, as clinical professionals also require other important features that relate to P and T waves to complete cardiac analysis and diagnosis. Due to the increasing complexity in signal processing algorithms, the consumed power and silicon areas increase significantly for corresponding hardware implementation. In accordance with the present embodiments, a robust ECG signal processing system has been described above that have a plurality of low complexity blocks to reduce power consumption and silicon area. The robust ECG signal processing system of the present embodiments can be on-chip and perform ECG signal processing including noise suppression, artificial baseline removal, clean ECG reconstruction, and heart beat rate (HBR) detection.

Furthermore, the robust ECG signal processing system in accordance with the present embodiments can perform ECG/cardiac features analysis that at least can realize the following functions: P and T waves peak detection; morphologies of P/QRS/T waves identification, including positive (+), negative (−), biphasic (+/− or −/+), only upwards, and only downwards; and the PR interval and RT interval calculation.

In the following description, in order to further substantially reduce power and area consumption, a sequential cardiac features analysis method is proposed to minimize the operation clock frequency and maximally reuse the hardware resource to reduce the required silicon area.

Figure 8:
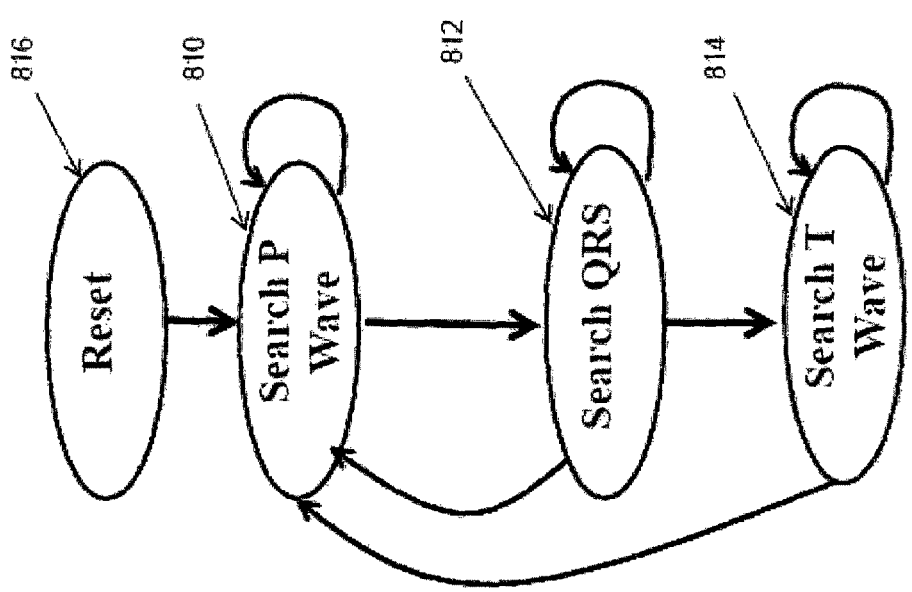
FIG. 8 depicts a flowchart of remote and/or on-chip cardiac features searching, i.e. P wave, QRS complex and T wave analysis, in accordance with the present embodiments.

Referring to FIG. 8, at least by virtue of the facts that P wave, QRS complex, and T wave occur sequentially in an ECG/cardiac signal, and that their analysis procedures appear similar because of the similar procedures of onset/peak/end point detection and morphology identification, a flowchart 800 of a processing flow of on-chip ECG features searching in accordance with the present embodiment is depicted, which constitutes a first level of the sequential cardiac features analysis.

As shown in FIG. 8, the DSPE in accordance with the present embodiment that comprises P/QRS/T features extraction block starts with step 810 "Search P wave". If there are no points of interest appearing, the DSPE stays at this step. Once the ECG processing system overall operates in high frequency, i.e., DHPF_S2 is larger than THf, the DSPE starts to search QRS complex. During step 812 "Search QRS", similarly, if there are no points of interest appearing, the DSPE stays at this step. Once QRS complex is identified, the DSPE starts with step 814 to search T wave; otherwise it will go back to the "search P wave" step 810 if there are no points of interest appearing after certain pre-defined number of samples. During step "Search T wave" 814, similarly, if there are no points of interest appearing, the DSPE stays at this step. Once T wave is identified or there are no points of interest appearing after certain pre-defined number of samples, the system will be reset 816 and go back to the "Search P wave" step 810 to search the next P wave. At each step of FIG. 8, there are detailed procedures for each morphology identification and features extraction, which constitute a second level of the sequential cardiac features analysis. The detailed procedures for each morphology identification and features extraction of P wave, QRS complex and T wave are shown in FIGS. 9-11.

Figure 9A:
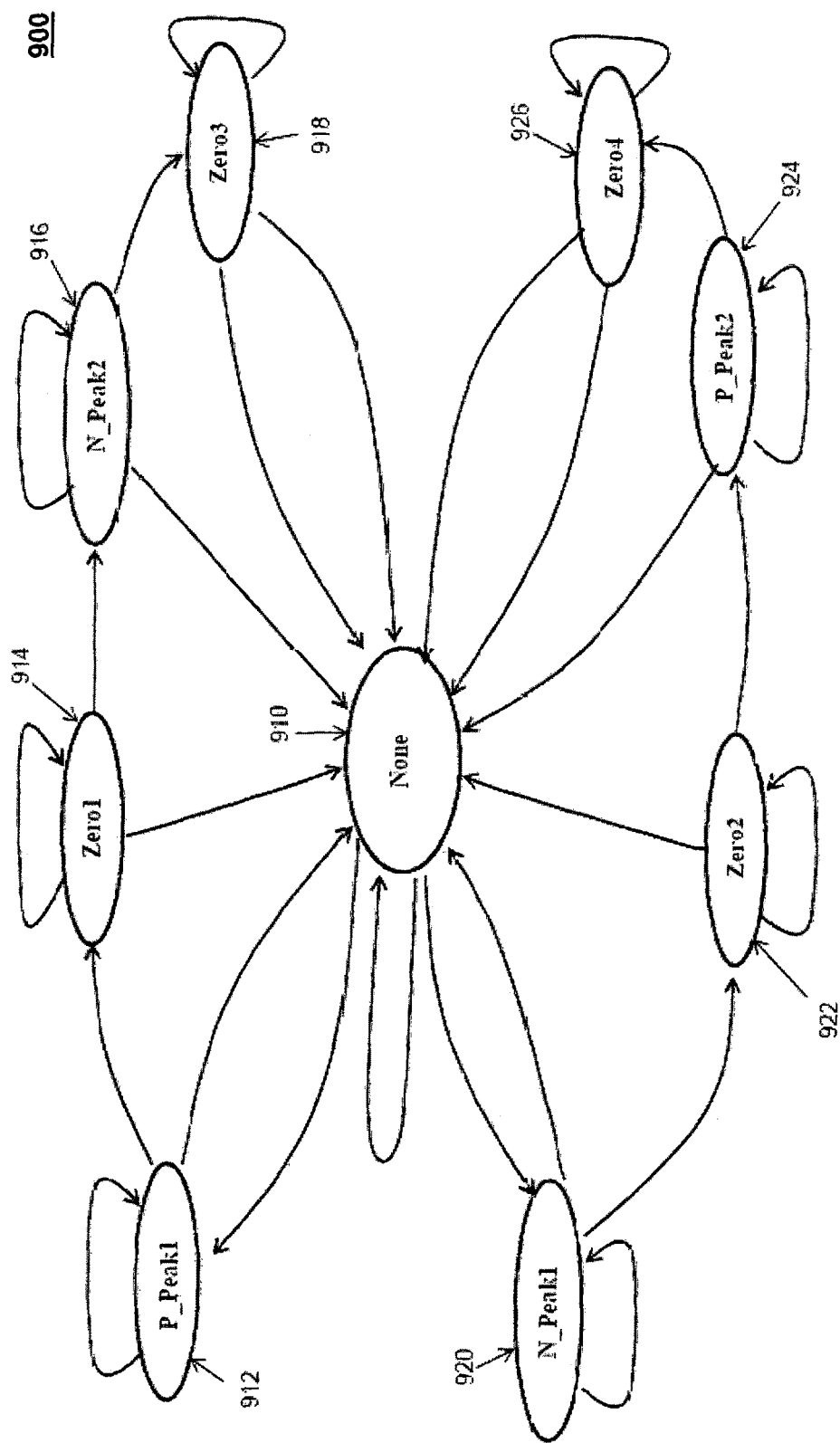
FIG. 9A depicts a processing flow illustrating the P wave identification and feature extraction in accordance with the present embodiments.

FIG. 9A shows a processing flow 900 for P wave identification and feature extraction. According to FIGS. 9B-9C, the morphologies of P wave includes positive P wave (P+) 960, negative P wave (P−) 962, and biphasic P waves (P+/−, P−/+) (not shown). DHPF_S4 can be used as the signal inputs in the present embodiment, because in comparison with DHPF outputs of other scales, it contains less high frequency noise as well as reduced baseline drifting, and contains major components of the P wave when the present embodiment samples at the second frequency f2 of 250 Hz.

In accordance with the P wave identification and feature extraction, the DSPE starts with the first step "None" 910, and then compares the input signal x with a pre-defined threshold THpp. If the input signal x is greater than THpp, it means that a positive peak of DHPF_S4 is to be appeared, indicating that the slope of DLPF_S3 increases fast. Thus, the DSPE proceeds to step "P_Peak1" 912.

During the "P_Peak1" step 912, the zero crossing point is searched, which corresponds to the peak value of DLPF_S3. A counter continuously counts the number of samples. If the zero-crossing point is detected, the DSPE proceeds to step "Zero1" 914, and the counter is reset. On the other hand, if there are no points of interest, and the counter exceeds a pre-defined value φpp, the DSPE will go back to step "None" 910 and compare the input x with THpp again.

During "Zero1" 914, the input signal x is compared with a pre-defined threshold THpn. The counter continuously counts the number of samples. If the input signal is smaller than THpn, it means that a negative peak of DHPF_S4 is to be appeared, indicating the slope of DLPF_S3 decreases fast. The DSPE thus proceeds to "N_Peak2" 916, and the counter is reset. On the other hand, if there are no points of interest, and the counter exceeds a pre-defined value φpz, the DSPE will go back to "None" 910.

During "N_Peak2" 916, the zero crossing point is searched, which corresponds to the negative peak value of DLPF_S3. A counter continuously counts the number of samples. If the zero crossing point is detected, the DSPE goes to "Zero3" 918, and the counter is reset. On the other hand, if there are no points of interest, and the counter exceeds a pre-defined value, φpd, the DSPE confirms that a positive P wave (P+) is detected. The DSPE will then go back to "None" 910, and the first level of the sequential cardiac features analysis as shown in FIG. 8 will go to the "Search QRS" step 812.

During "Zero3" 918, the input signal x is compared with a pre-defined threshold THpp. The counter continuously counts the number of samples. If the input signal is greater than THpp, a positive peak is to be appeared. Thus, the DSPE switches back to "None" 910, and the counter is reset. At the same time, the DSPE can confirm that the biphasic P wave (+/−P) is identified. On the other hand, if there are no points of interest detected, and the counter exceeds a pre-defined value φpd, the DSPE confirms that a positive P wave (P+) is detected. The DSPE will then go back to "None" 910, and the first level of the sequential cardiac features analysis as shown in FIG. 8 will go to "Search QRS" step 812.

Similar as the aforementioned procedure, the morphologies of a negative P wave (P−) and its biphasic −/+P can be identified by detecting "N_Peak1" 920, "Zero2" 922, "P_Peak2" 924, and "Zero4" 926, as shown at the bottom half portion of FIG. 9A.

Figure 10A:
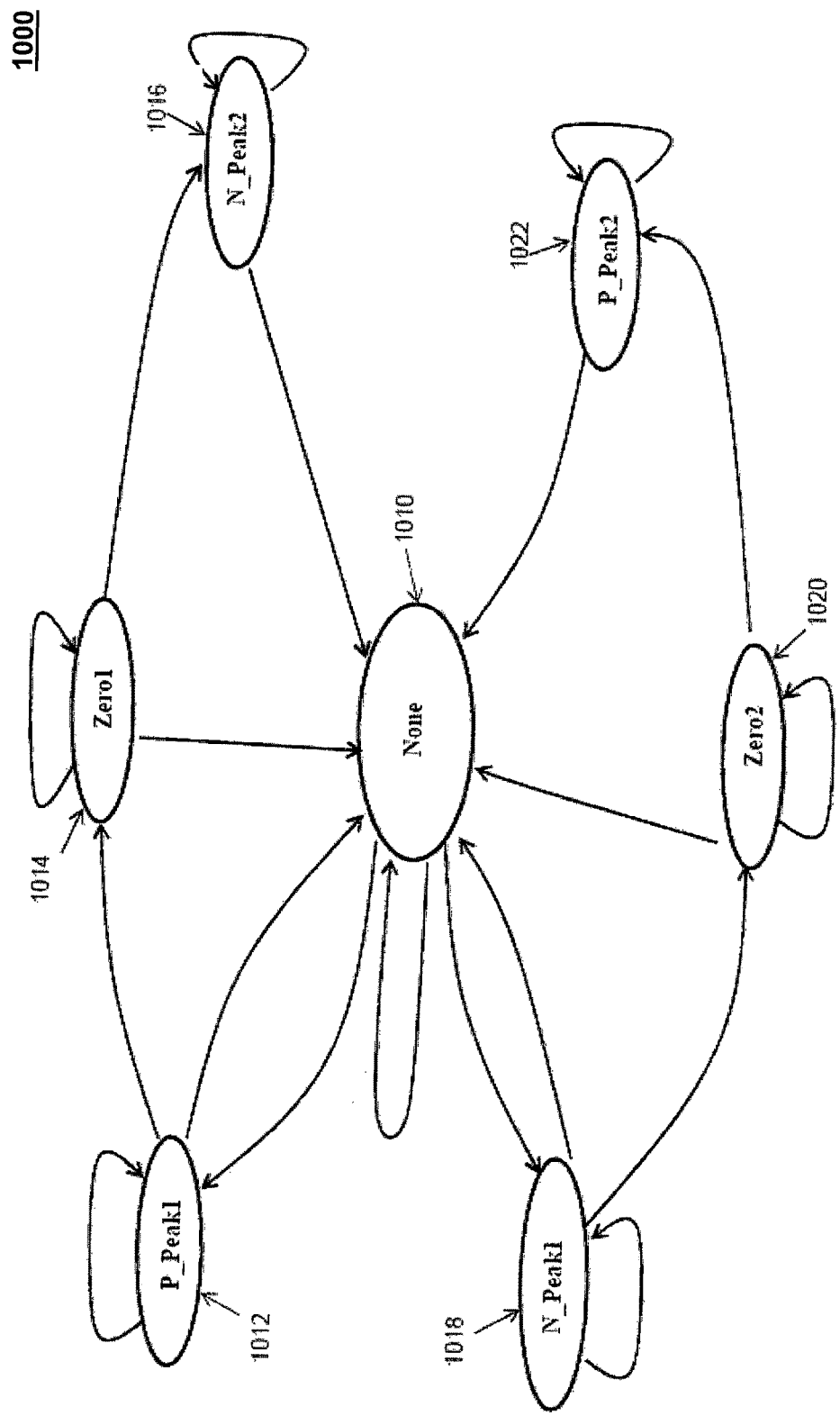
FIG. 10A depicts a processing flow illustrating the QRS complex identification and feature extraction in accordance with the present embodiments.
Figures 10B, 10C:
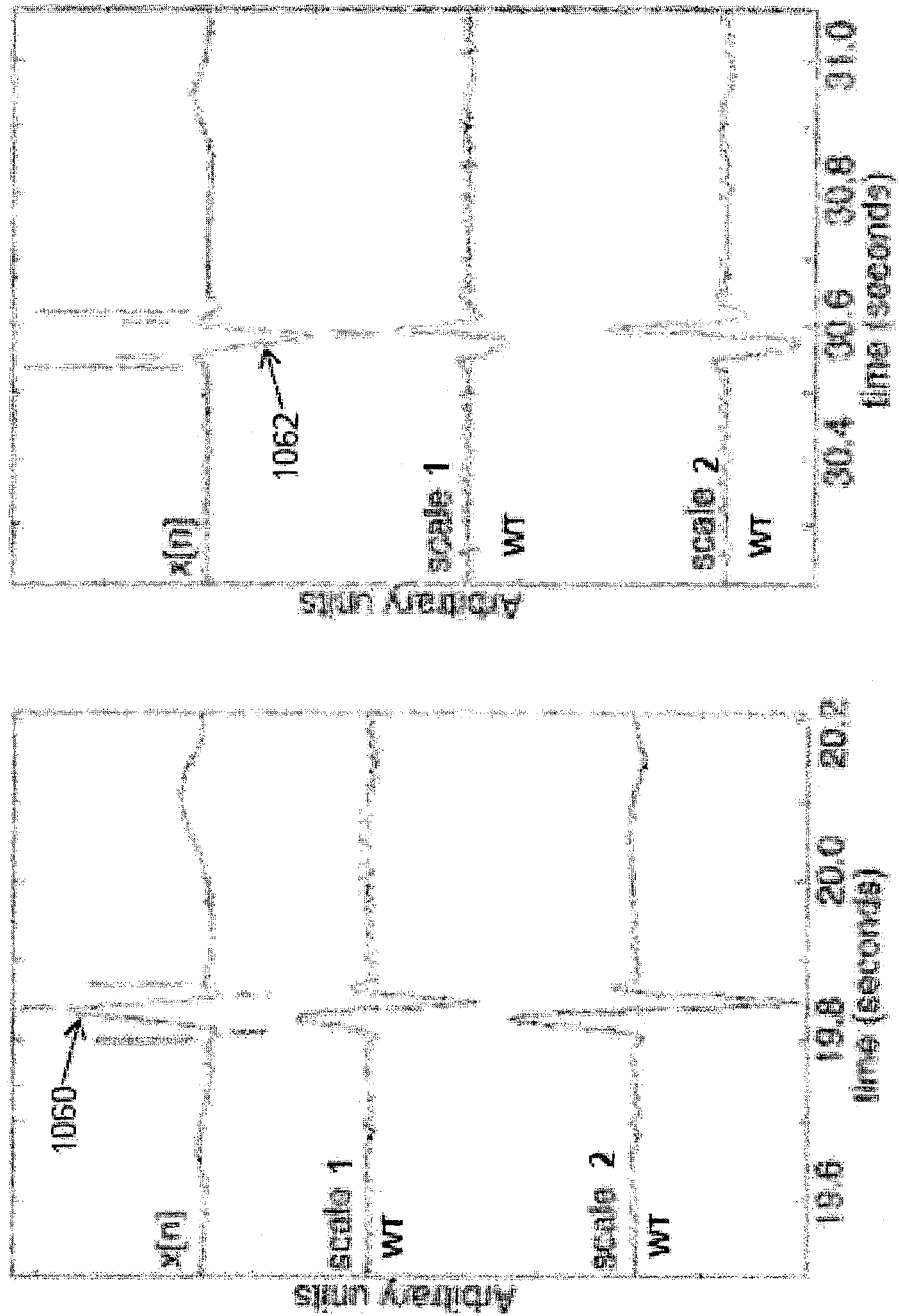
FIGS. 10B-10C depict morphologies of QRS complex, including positive QRS wave (QRS+) and negative QRS wave (QRS−), in accordance with the present embodiments.

The processing flow of QRS complex identification and feature extraction is similar to P wave identification and feature extraction. Referring to FIG. 10A, a graph 1000 represents the corresponding processing flow. For the QRS complex, the morphologies of positive QRS wave (QRS+) 1060 and negative QRS wave (QRS−) 1062 are distinguished and depicted in FIGS. 10B-10C. DHPF_S4 is also adopted as the signal inputs because when searching QRS complex at the first frequency f1 of 500 Hz, the bandwidth of DHPF_S4 is around 8-27 Hz, as shown in FIG. 4.

The first status of QRS complex identification and feature extraction is set as "None" 1010, and the input signal is compared with a pre-defined threshold THqp. If the input signal is higher than THqp, it indicates that the slope of DLPF_S3 increases fast, and thus the status switches to "P_Peak1" 1012.

At "P_Peak1" step 1012, the zero crossing point is searched, which corresponds to the peak value of DLPF_S3. A counter continuously counts the number of samples. If the zero crossing point is detected, the DSPE goes to "Zero1" 1014, and the counter is reset. On the other hand, if there are no points of interest, and the counter exceeds a pre-defined value φqp, the DSPE will go back to "None" 1010 and compare the input signal with THqp again.

At "Zero1" step 1014, the input signal is compared with a pre-defined threshold THqn. The counter continuously counts the number of samples. If the input signal is lower than THqn, it means that the slope of DLPF_S3 decreases fast. The status then switches to "N_Peak2" 1016, and the counter is reset. On the other hand, if there are no points of interest, and the counter exceeds a pre-defined value φqz, the processing flow will go back to "None" 1010.

At "N_Peak2" step 1016, the counter continuously counts the number of samples. When the counter exceeds a pre-defined value φqd, the system confirms that a positive QRS complex (QRS+) is detected. The processing flow will go back to "None" 1010, and the on-chip ECG features searching flow as shown in FIG. 8 will go to "Search T wave" step 814.

Similar as the aforementioned procedure, the morphologies of a negative QRS (QRS−) wave can be identified by detecting the status of "N_Peak1" 1018, "Zero2" 1020, and "P_Peak2" 1022, as shown at the bottom half portion of FIG. 10A.

Figure 11A:
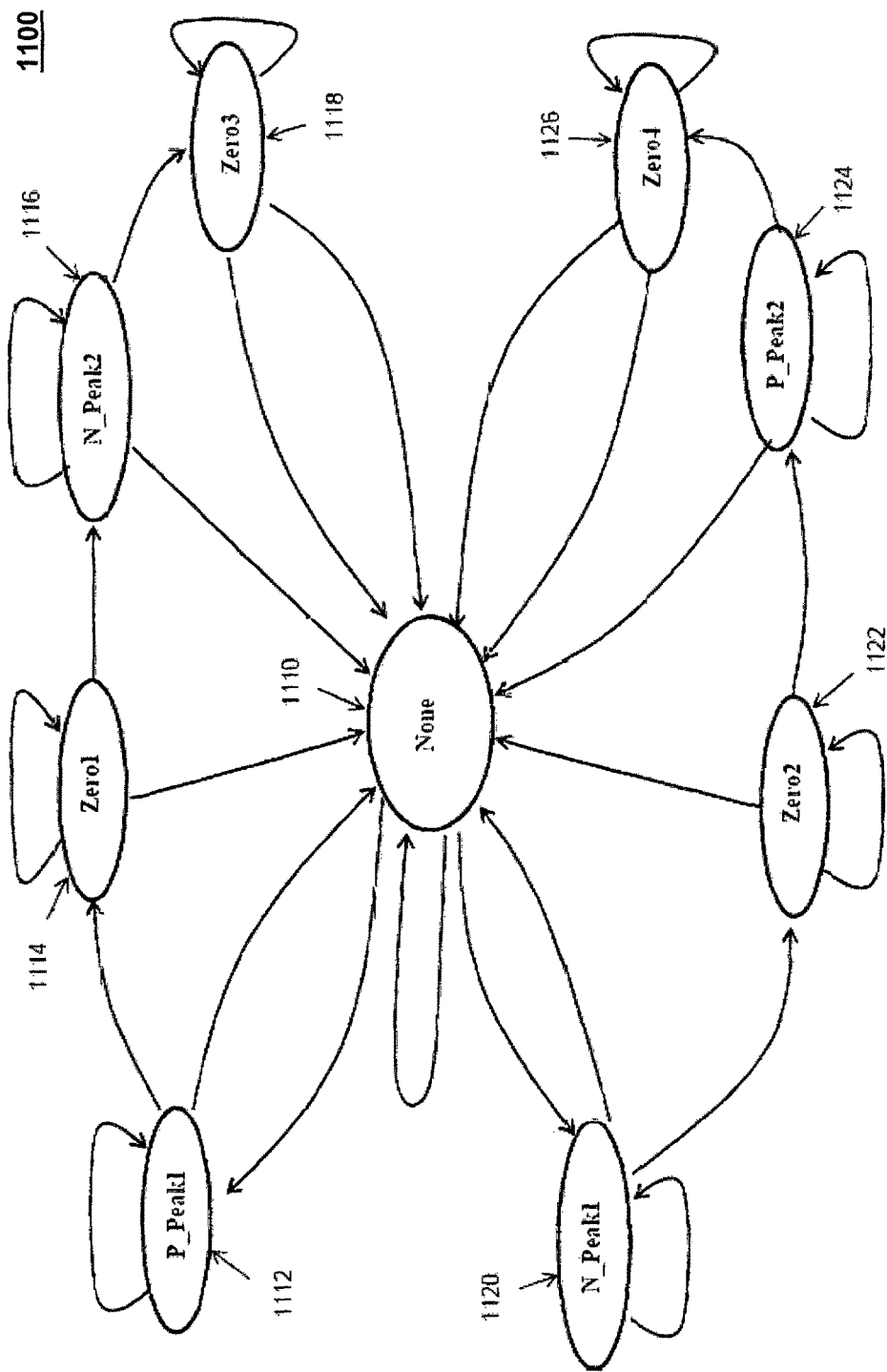
FIG. 11A depicts a processing flow illustrating the T wave identification and feature extraction in accordance with the present embodiments.

Referring to FIG. 11A, a graph 1100 of the processing flow for T wave identification and feature extraction is represented, which is similar as the ones for P wave and QRS complex. For the T wave, the morphologies including upwards T wave 1166, downwards T wave 1168, positive T wave (T+) 1160, negative T wave (T−) 1162, and biphasic T wave (T+/−, T−/+) 1164 are depicted in FIGS. 11B-11F. DHPF_S4 is again adopted as the signal inputs, for similar reasons as described above for the P wave identification and feature extraction.

The first status of the T wave identification and feature extraction is set as "None" 1110. The input signal is compared with a pre-defined threshold THtp. If the input signal is greater than THtp, it indicates that the slope of DLPF_S3 increases fast, and thus the processing flow switches to "P_Peak1" 1112.

At "P_Peak1" step 1112, the zero crossing point is searched, which corresponds to the peak value of DLPF_S3. A counter continuously counts the number of samples. If the peak is detected, the processing flow goes to "Zero1" 1114, and the counter is reset. On the other hand, if there are no points of interest, and the counter exceeds a pre-defined value φtp, the processing flow will go back to "None" 1110 and compare input signal with THtp again.

At "Zero1" step 1114, the input signal is compared with a pre-defined threshold THtn. The counter continuously counts the number of samples. If the input signal is lower than THtn, it means that the slope of DLPF_S3 decreases fast. The status switches to "N_Peak2" 1116, and the counter is reset. On the other hand, if there are no points of interest, and the counter exceeds a pre-defined value φtd, it is confirmed that the upwards T wave is identified. The processing flow will go back to "None" 1110, and the processing of T wave identification and feature extraction is completed.

At "N_Peak2" step 1116, the DSPE searches the zero-crossing point, and the counter continuously counts the number of samples. If the zero-crossing point is found, the processing flow goes to "Zeros3" 1118. On the other hand, when the counter exceeds a pre-defined value φtd, it is confirmed that a positive T wave (T+) 1160 is detected. The processing flow will go back to "None" 1110, the processing of T wave identification and feature extraction is completed.

At "Zero3" step 1118, the input signal compares with a pre-defined threshold THtp. The counter continuously counts the number of samples. If the input signal is higher than THtp, it is confirmed that the biphasic (+/−) T wave 1164 is identified. On the other hand, if there are no points of interest, and the counter exceeds a pre-defined value φtd, the DSPE confirms that a positive T wave 1160 is detected. The processing flow will go back to "None" 1110, the processing of T wave identification and feature extraction is completed.

Similar as the aforementioned procedure, the morphologies of negative T (T−) 1162 and biphasic −/+T 1164 can be identified by detecting the status of "N_Peak1" 1120, "Zero2" 1122, "P_Peak2" 1124, and "Zero4" 1126, as shown at the bottom half portion of FIG. 11A.

It can be observed from FIGS. 9-11 that the proposed ECG features identification and extraction for P/QRS/T waves in accordance with the present embodiment have similar analysis procedures. Specifically, all the state machines can be represented by at most 9 statuses, and the statuses transactions are similar with same conditions and different outputs. Furthermore, since the analysis of P, QRS, and T are in sequence in the present embodiment, most of the resource for these statuses transactions can be shared, which is highly recommended for low power hardware implementation. In the present embodiment, pipeline structure is adopted for the distribution of the P, QRS and T analysis, so that the required highest operation frequency is the same as the input sampling rate.

Some existing on-chip ECG processors are based on software programming, as disclosed in "A Wearable BSN-based ECG-recording System Using Micromachined Electrode for Continuous Arrhythmia Monitoring" by D. G. Guo, et al, on *Proc. IEEE 5th International Workshop on Wearable and Implantable Body Sensor Networks*, June 2008, pp. 41-44; and in "An ultra low energy biomedical signal processing system operating at near-threshold" by J. Hulzink, et al, on *IEEE Transactions on Biomedical Circuits and Systems*, December 2011, vol. 5, pp. 546-554. They have more flexibilities to achieve multiple functions, but have lower energy efficiency due to the software operation in sequence. On the other hand, some of the research present the application-specific ECG processing ASIC. Due to high computational complexity, the functions that they can achieve are limited, and most of them mainly focus on the QRS detection and heart beat rate (HBR) calculation. As discussed above, in cardiac monitoring and clinical treatments, critical information related to P and T waves are also required. Therefore, the present on-chip ECG processing system in accordance with the present embodiments outperforms other existing schemes in terms of both high energy efficiency and comprehensive functions.

It should be emphasized that dynamic system operation frequencies between 250 Hz and 500 Hz are adopted in the herein described present embodiment. Therefore, in order to reduce the hardware complexity, although only DHPF_S4 is used for all the processing, the actual signal components used for P/T analysis and QRS analysis are different, as shown in FIG. 4.

As described herein, the high frequency noise suppression and baseline drifting removal are also included in the present embodiments. It would be appreciated to the skilled person in the art that the adaptive threshold-based noise suppression is preferably applied to the DHPF outputs of Scale 1-3 of the present embodiments.

Figure 12:
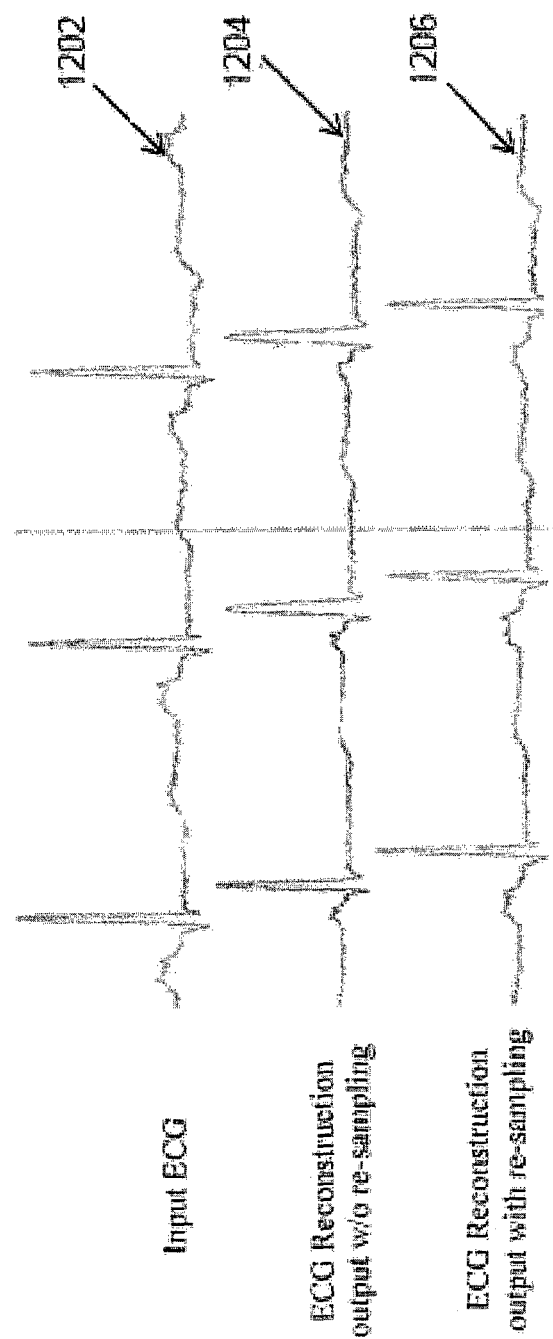
FIG. 12 depicts signaling patterns illustrating separate stimulation results of ECG reconstruction outputs in accordance with the present embodiments as shown in FIG. 1 and FIG. 3.

Referring to FIG. 12, a graph 1200 illustrating stimulation results of ECG reconstruction outputs using adaptive system operation clock with or without re-sampling is present. In more details, FIG. 12 presents the input ECG signal 1202, the reconstruction ECG output without re-sampling 1204, and the ECG reconstruction output with re-sampling 1206. In order to verify the functionality and compare the reconstruction signals with original input, only the WT decomposition followed by WT reconstruction is performed, without interference suppression and baseline drifting removal. It can be observed from FIG. 12 that if there is no re-sampling, the adaptive system operation clock of the output signal is improper, and thus there will be distortion in the shape of the ECG reconstruction output 1204. However, by virtue of the provided synchronization output buffer 316 with output sampling clock generator 318 (as shown in FIG. 3), the correct ECG reconstruction output 1206 can be obtained as shown in FIG. 12, which matches the original ECG input signal 1202 very well.

Figure 13:
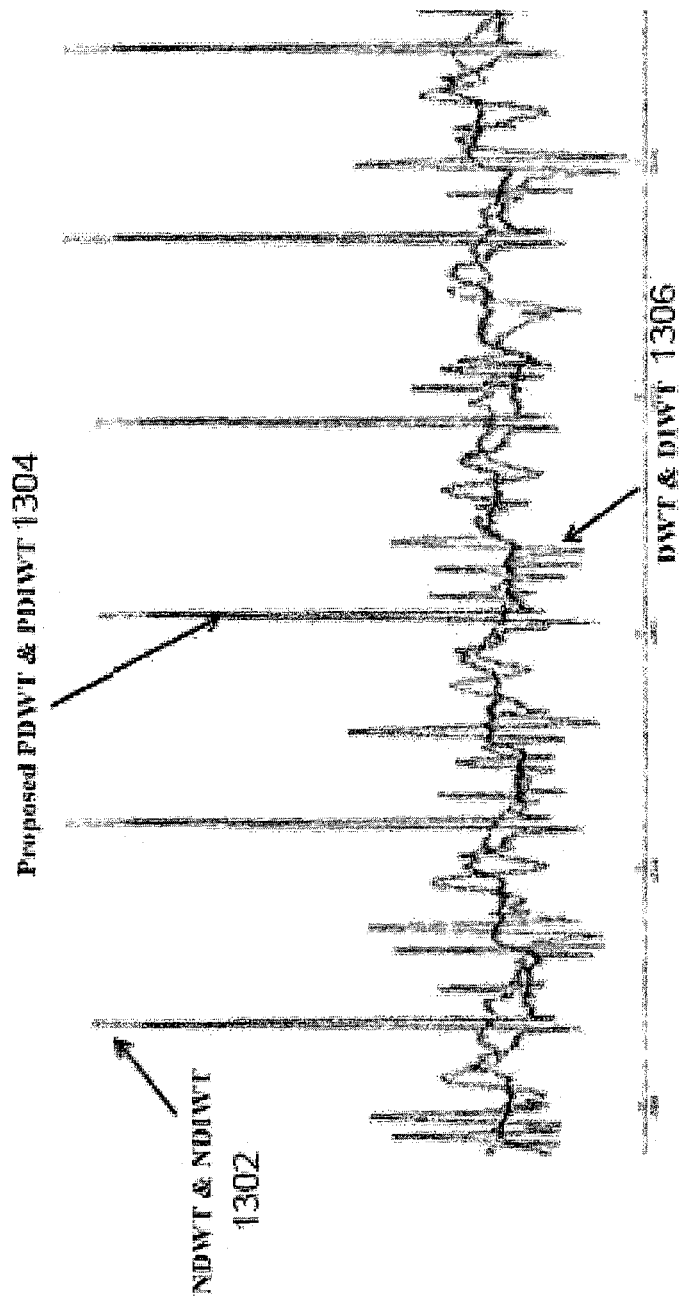
FIG. 13 depicts a graph illustrating combined stimulation results of ECG reconstruction outputs of the non-downsampling WT & IWT scheme, the proposed Pseudo-downsampling WT & IWT with adaptive storing scheme, and downsampling WT & IWT scheme in accordance with the present embodiments.

Referring to FIG. 13, a graph 1300 is present illustrating combined stimulation results of ECG reconstruction output of the non-downsampling WT & IWT (NDWT & NDIWT) scheme 1302, the proposed pseudo-downsampling WT & IWT (PDWT & PDIWT) and adaptive storing scheme 1304, and the downsampling WT & IWT (DWT & DIWT) scheme 1306, respectively. It should be noted that the reconstruction output of NDWT & NDIWT 1302 is the optimal result because it is close to the original ECG inputs. According to FIG. 13, it can be observed that the provided PDWT scheme can obtain suboptimal results 1304 as compared with NDWT & NDIWT scheme. On the other hand, it can be observed that the output of the DWT & DIWT scheme 1306 is distorted and cannot obtain the correct ECG reconstruction output.

Figure 14:
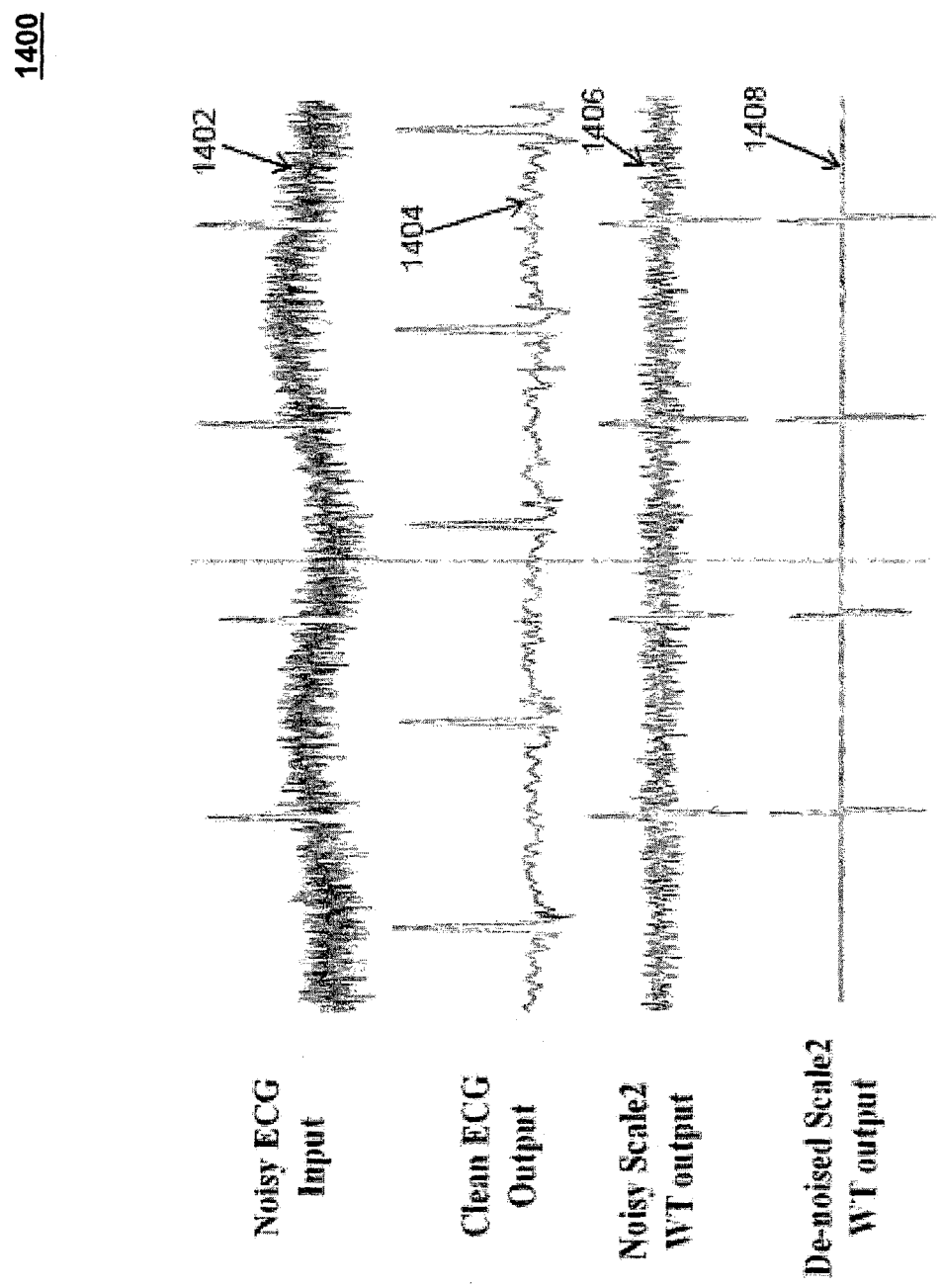
FIG. 14 depicts signaling patterns illustrating stimulation results of ECG reconstruction in accordance with the present embodiments, both had the proposed interference/noise suppression and baseline drifting removal carried on. Scale 2 WT outputs before and after noise suppression are also depicted.

Referring to FIG. 14, a graph 1400 is depicted to illustrate stimulation results of clean ECG reconstruction 1404, had both the proposed interference/noise suppression and baseline drifting removal carried on in accordance with the present embodiments. Scale 2 WT outputs, before 1406 and after 1408 noise suppression, are also depicted. It can be observed that the ECG input signal 1402 and the Scale 2 WT output 1406 are distorted by high frequency noise as well as low frequency baseline drifting. It can also be observed from the stimulation results 1404 and 1408 that the reconstructed ECG signal and de-noised Scale 2 WT output are clean after noise suppression and baseline drifting removal.

Figure 15:
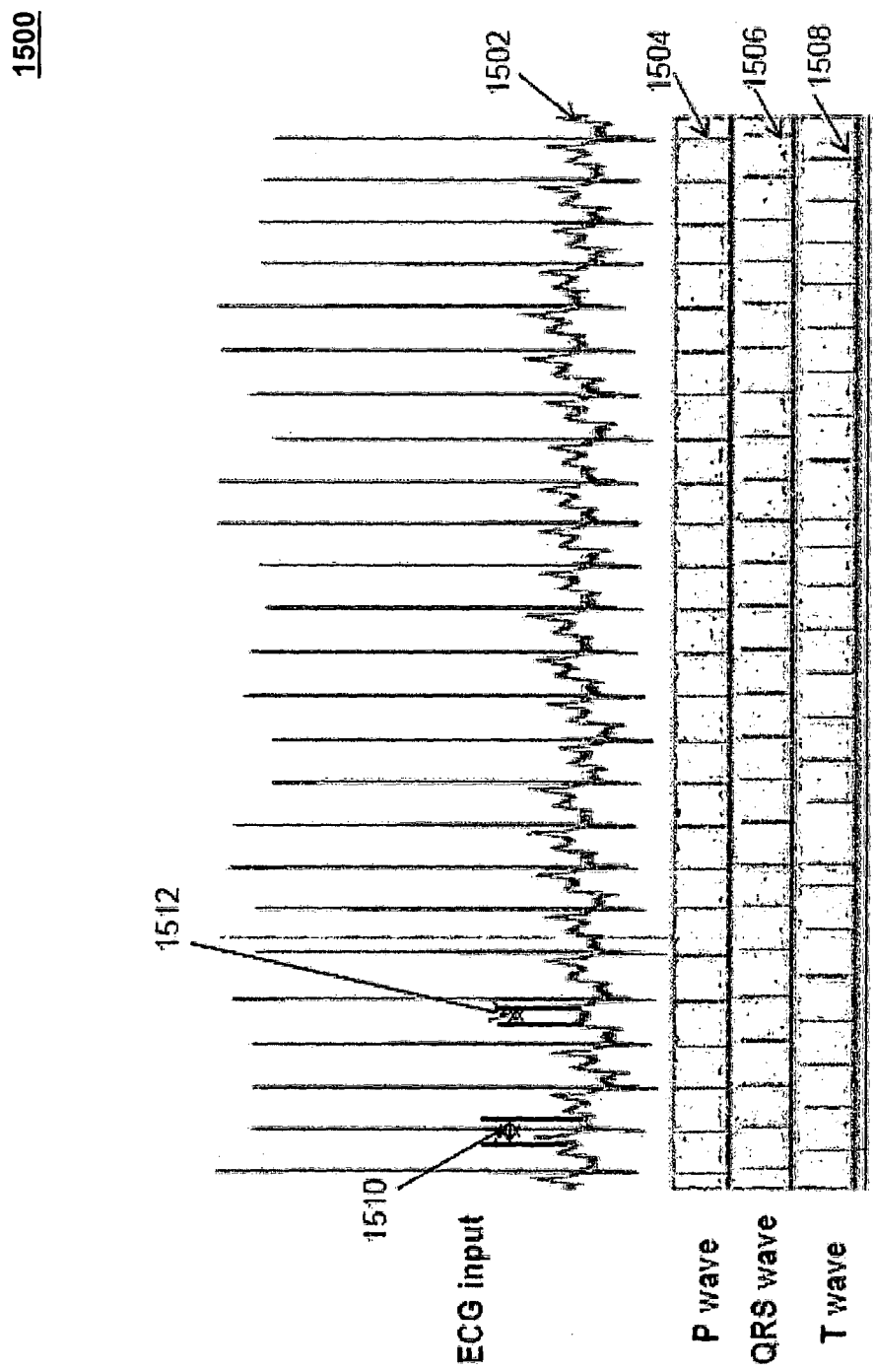
FIG. 15 depicts a plurality of stimulation results of the proposed cardiac features extraction in accordance with the embodiments shown in FIGS. 8-11, including indicators of P wave, QRS complex and T waves.

Referring to FIG. 15, a graph 1500 of a plurality of stimulation results of the discussed cardiac feature extraction of the ECG input 1502 is depicted in accordance with the embodiments shown in FIGS. 8-11, including indicators of P wave, QRS complex and T waves. Extracted indicators of P wave 1504, QRS complex 1506 and T waves 1508 are presented in FIG. 15. It can be observed that all these features are extracted accurately. Therefore, more cardiac features such as QT interval 1510 and PR interval 1512 can be accurately calculated.

As described herein, a real-time multi-functional ECG signal processing system with high energy and area efficiency, a digital signal processing engine (DSPE) for the ECG signal processing system, and a method for processing ECG signals are provided in the present invention. It achieves high energy-efficiency by adopting several innovative techniques, including adaptive system operation clocking for overall system, pseudo-downsampling WT & IWT, adaptive storing, and run-length compression with noise suppression. Furthermore, low-complexity cardiac features analysis schemes are proposed to extract sufficient critical cardiac features for long-term cardiac monitoring and clinical treatment. In view of the above, the real-time multi-functional ECG signal processing system with high energy and area efficiency, the DSPE for the ECG signal processing system and the method for processing ECG signals are highly suitable for wearable sensor applications of long-term cardio-vascular monitoring.

We claim:

1. An electrocardiogram (ECG) signal processing system, the ECG signal processing system comprising:

an analog-to-digital converter (ADC) operable for sampling an input analog ECG signal at a first frequency $f_1$ and a second frequency $f_2$ to convert the input analog ECG signal into a digital ECG signal;

a digital signal processing engine (DSPE) coupled to the ADC to receive the digital ECG signal, the DSPE being configured to sample the digital ECG signal at the first frequency $f_1$ and the second frequency $f_2$ to decompose and reconstruct the digital ECG signal; and a dynamic system clock source coupled to the ADC and the DSPE for dynamic adaptive signal sampling, the dynamic system clock source clocking the ADC and the DSPE at the first frequency $f_1$ to detect one or more first parameters of the input analog ECG signal and at the second frequency $f_2$ to detect one or more second parameters of the input analog ECG signal, wherein the DSPE comprises:

a wavelet transformation (WT) unit, the WT unit comprising a plurality of scales, wherein the WT unit is adapted to decompose the digital ECG signal into a plurality of wavelets, each wavelet being output from one of the plurality of scales; and a plurality of signal processing blocks, each of the signal processing blocks coupled to one or more outputs of the plurality of scales and configured to receive and process the one or more wavelets from the respective outputs, wherein the signal processing blocks provide processing functions which differ from one another, wherein the plurality of signal processing blocks comprise a cardiac features extraction block, the cardiac features extraction block receiving a high pass filtering of a predetermined one of the plurality of scales, wherein the cardiac features extraction block is configured to process a QRS complex extraction when the dynamic system clock source is clocking the ADC and the DSPE at the first frequency $f_1$, and to process P wave extraction and T wave extraction when the dynamic system clock source is clocking the ADC and the DSPE at the second frequency $f_2$.

2. The ECG signal processing system of claim 1, wherein the ECG signal processing system is configured to detect a QRS complex when $f_1$ is 500 Hz, and wherein the plurality of scales comprises six scales, the plurality of scales having 3 dB bandwidths of around 125 to 250 Hz; 62.5 to 125 Hz; 18 to 58.5 Hz; 8 to 27 Hz; 4 to 13.5 Hz; and 2 to 6.5 Hz for the first to the sixth scales respectively, when the dynamic system clock source is clocking at the first frequency $f_1$.

3. The ECG signal processing system of claim 1, wherein the ECG signal processing system is configured to detect P and T waves when $f_2$ is 250 Hz, and wherein the plurality of scales comprises six scales, the plurality of scales having 3 dB bandwidths of around 62.5 to 125 Hz; 18 to 58.5 Hz; 8 to 27 Hz, 4 to 13.5 Hz; 2 to 6.5 Hz; and 1 to 3.25 Hz for the first to the sixth scales respectively, when the dynamic system clock source is clocking at the second frequency $f_2$.

4. The ECG signal processing system of claim 1, wherein the WT unit comprises a plurality of low pass filters (LPF) and a plurality of high pass filters (HPF), and wherein the plurality of signal processing blocks further comprises a baseline drifting removal unit, the baseline drifting removal unit being coupled to the respective outputs of the high pass filters of the fifth and sixth scales and the output of the low pass filter of the sixth scale.

5. The ECG signal processing system of claim 4, wherein the dynamic system clock source is switched between $f_1$ and $f_2$ by a multiplexer, the multiplexer being controlled by a comparison between output of the high pass filter on the second scale and a threshold $TH_f$, and wherein the multiplexer switches to the first frequency $f_1$ when the output of the high pass filter on the second scale exceeds the threshold $TH_f$.

6. The ECG signal processing system of claim 4, wherein the predetermined one of the plurality of scales comprises the fourth scale, and wherein the cardiac features extraction block is coupled to the output of the high pass filter of the fourth scale.

7. The ECG signal processing system of claim 4, wherein the plurality of signal processing blocks comprise an ECG signal reconstruction block, and wherein the ECG signal reconstruction block is coupled to outputs of high pass filters of the first to the fourth scales and the outputs of the baseline drifting removal unit, wherein the ECG signal reconstruction block is configured to synchronize and output signals belonging to the high pass filtered components of the first to the sixth scales and the low pass filtered component of the sixth scale.

8. The ECG signal processing system of claim 1, wherein the ADC is a successive approximation (SAR) ADC.

9. A digital signal processing engine (DSPE) for ECG signal processing, the DSPE being coupled to a digital ECG signal input and comprising:

a wavelet transformation (WT) unit, the WT unit comprising a plurality of scales, wherein the WT unit is adapted to decompose the digital ECG signal into a plurality of wavelets, each wavelet being output from one of the plurality of scales; and a plurality of signal processing blocks, each of the signal processing blocks coupled to one or more outputs of the plurality of scales and configured to receive and process the one or more wavelets from the respective outputs, wherein the signal processing blocks provide processing functions which differ from one another;

wherein the WT unit and the plurality of signal processing blocks are coupled to a dynamic system clock source for dynamic signal sampling, the dynamic system clock source clocking the DSPE at a first frequency $f_1$ to detect one or more first parameters of the input digital ECG signal and at a second frequency $f_2$ to detect one or more second parameters of the input digital ECG signal, wherein the dynamic system clock source is switched between $f_1$ and $f_2$ by a multiplexer, the multiplexer being con rolled by a comparison between an output of a high pass filter on a predetermined one of the plurality of scales and a threshold $TH_f$, wherein the multiplexer switches to the first frequency $f_1$ when the output of the high pass filter on the predetermined one of the plurality of scales exceeds the threshold $TH_f$.

10. The DSPE of claim 9, wherein the plurality of scales comprises a plurality of cascaded scales, each of the plurality of cascaded scales having a different bandwidth, and wherein a wavelet output from one of the cascaded scales is derived from a wavelet output from an earlier one of the plurality of cascaded scales.

11. A digital signal processing engine (DSPE) for ECG signal processing, the DSPE being coupled to a digital ECG signal input and comprising:

a wavelet transformation (WT) unit, the WT unit comprising a plurality of scales, wherein the WT unit is adapted to decompose the digital ECG signal into a plurality of wavelets, each wavelet being output from one of the plurality of scales; and a plurality of signal processing blocks, each of the signal processing blocks coupled to one or more outputs of the plurality of scales and configured to receive and process the one or more wavelets from the respective outputs, wherein the signal processing blocks provide processing functions which differ from one another;

wherein the WT unit and the plurality of signal processing blocks are coupled to a dynamic system clock source for dynamic signal sampling, the dynamic system clock source clocking the DSPE at a first frequency $f_1$ to detect one or more first parameters of the input digital ECG signal and at a second frequency $f_2$ to detect one or more second parameters of the input digital ECG signal and wherein the WT unit comprises a plurality of low pass filters (LPF) and a plurality of high pass filters (HPF) and wherein the dynamic system clock source is switched between $f_1$ and $f_2$ by a multiplexer, the multiplexer being controlled by a comparison between an output of a high pass filter on a second one of the plurality of scales and a threshold $TH_f$, wherein the multiplexer switches to the first frequency $f_1$ when the output of the high pass filter on the second one of the plurality of scales exceeds the threshold $TH_f$.

12. The DSPE of claim 11, wherein the plurality of signal processing blocks comprise at least one noise suppression block.

13. The DSPE of claim 12, wherein each of the at least one noise suppression block comprises at least one threshold-based de-nosing unit, each of the at least one threshold-based de-nosing unit being coupled to one of the respective outputs of the WT unit emitting wavelets coupled to the first three of the plurality of scales, and wherein the output of a high pass filter smaller than an adaptive threshold is forced to zero.

14. A method for processing an ECG signal comprising:
providing a first device operable to sample an input ECG signal at a first frequency $f_1$ and a second frequency $f_2$ and configured to convert the input ECG analog signal into a digital ECG signal;
providing a second device coupled to the first device to receive the digital ECG signal, the second device being configured to sample the digital ECG signal at the first frequency $f_1$ and the second frequency $f_2$ to decompose and reconstruct the digital ECG signal; and
providing a dynamic clock source connected to the first and the second device, wherein the dynamic clock source clocks the first and the second devices at the first frequency $f_1$ to detect one or more first parameters of the input analog ECG signal and at the second frequency $f_2$ to detect one or more second parameters of the input analog ECG signal,
providing a wavelet transformation (WT) unit, the WT unit comprising a plurality of scales, wherein the WT unit is adapted to decompose the digital ECG signal into a plurality of wavelets, each wavelet being output of one of the plurality of scales;
providing a plurality of signal processing blocks, each of the sign processing blocks coupled to one or more outputs of the plurality of scales and configured to receive and process the one or more wavelets from the respective outputs, wherein the signal processing blocks provide processing function which differ from one another, and wherein the plurality of signal processing blocks comprise a cardiac features extraction block; and
the cardiac features extraction block receiving a high pass filtering of a predetermined one of the plurality of scales for extracting a QRS complexes when the dynamic system clock source is clocking the ADC and the DSPE at the first frequency $f_1$, and for extracting P waves and T waves when the dynamic system clock source is clocking the ADC and the DSPE at the second frequency $f_2$.

15. The method for processing the ECG signal of claim 14, wherein the method comprises detecting a QRS complex when $f_1$ is 500 Hz.

16. The method for processing the ECG signal of claim 14, wherein the method comprises detecting P and T waves when $f_2$ is 250 Hz.

17. The method for processing the ECG signal of claim 14, wherein the operation of providing the WT unit comprises providing a plurality of low pass filters (LPF), a plurality of high pass filters (HPF), and at least one storage unit.

* * * * *